(12) United States Patent
Kampshof et al.

(10) Patent No.: US 12,411,119 B2
(45) Date of Patent: Sep. 9, 2025

(54) IN-LINE SENSOR, MILKING CLUSTER AND ASSOCIATED METHODS

(71) Applicant: BOVONIC LIMITED, Tauranga (NZ)

(72) Inventors: Liam George Kampshof, Tauranga (NZ); Gary Edwin Campbell, Tauranga (NZ)

(73) Assignee: BOVONIC LIMITED, Tauranga (NZ)

( * ) Notice: Subject to any disclaimer, the term of this patent is extended or adjusted under 35 U.S.C. 154(b) by 0 days.

(21) Appl. No.: 18/839,714

(22) PCT Filed: Feb. 17, 2023

(86) PCT No.: PCT/NZ2023/050018
§ 371 (c)(1),
(2) Date: Aug. 19, 2024

(87) PCT Pub. No.: WO2023/158323
PCT Pub. Date: Aug. 24, 2023

(65) Prior Publication Data
US 2025/0116644 A1    Apr. 10, 2025

(30) Foreign Application Priority Data

Feb. 18, 2022   (AU) .............................. 2022900361
Aug. 10, 2022   (AU) .............................. 2022902243

(51) Int. Cl.
*A01J 5/013*    (2006.01)
*A01J 11/02*    (2006.01)
(Continued)

(52) U.S. Cl.
CPC ............ *G01N 33/04* (2013.01); *A01J 5/0136* (2013.01); *A01J 11/02* (2013.01); *G01N 1/2035* (2013.01); *G01N 2001/2064* (2013.01)

(58) Field of Classification Search
CPC ................. G01N 33/04; G01N 1/2035; G01N 2001/2064; A01J 5/0136; A01J 11/02; A01J 5/16; A01J 5/10; A01J 5/0138
(Continued)

(56) References Cited

U.S. PATENT DOCUMENTS 2,898,549 A   8/1959  Miller
3,512,080 A   5/1970  Hanson
(Continued)

FOREIGN PATENT DOCUMENTS

AU    485902      3/1975
CA    2424629     10/2004
(Continued)

OTHER PUBLICATIONS

International Search Report and Written Opinion issued in PCT/NZ2023/050018 on Apr. 13, 2023.
(Continued)

*Primary Examiner* — Robert R Raevis
(74) *Attorney, Agent, or Firm* — ARC IP LAW, PC; Joseph J. Mayo

(57) ABSTRACT

Described herein is an in-line sensor for sensing properties of a pulsed milk flow on a continuous basis. A milking cluster comprising multiple pulsed milk flow inputs from lactating animal teats and a mixing point or claw for the multiple inputs is described that includes multiple in-line sensors for each pulsed milk flow input. Methods of use of the in-line sensor and milking cluster are also described. The in-line sensor described may be easily integrated into existing milking apparatus, is reliable, has a low cost, and is self-cleaning/self-emptying.

18 Claims, 21 Drawing Sheets

(51) Int. Cl.
*G01N 1/20* (2006.01)
*G01N 33/04* (2006.01)

(58) Field of Classification Search
USPC ....... 324/446, 438, 691, 693, 694, 697, 698; 73/64.56, 863, 863.41, 863.51, 864.81, 73/866.5; 374/141, 142, 208; 137/103
See application file for complete search history.

(56) References Cited

U.S. PATENT DOCUMENTS

| | | |
|---|---|---|
| 3,566,841 A | 3/1971 | Gerrish et al. |
| 3,664,306 A | 5/1972 | Quayle et al. |
| 3,874,337 A | 4/1975 | Umbaugh et al. |
| 4,156,179 A | 5/1979 | Stephen et al. |
| 4,325,028 A | 4/1982 | Takahashi |
| 4,391,222 A | 7/1983 | Icking et al. |
| 4,714,048 A | 12/1987 | Jefferies et al. |
| 4,771,007 A | 9/1988 | Tippetts et al. |
| 4,793,285 A | 12/1988 | Marshall |
| 5,080,040 A | 1/1992 | van der Lely et al. |
| 5,792,964 A * | 8/1998 | van den Berg ....... G01F 13/006 73/861.15 |
| 2002/0162509 A1 | 11/2002 | Hakes |
| 2008/0006210 A1 | 1/2008 | Springer et al. |
| 2009/0255473 A1 * | 10/2009 | Katz ..................... A23C 19/02 119/14.08 |
| 2012/0097107 A1 * | 4/2012 | Torgerson ............... A01J 5/007 119/14.08 |
| 2021/0239671 A1 | 8/2021 | Suhr et al. |
| 2021/0360891 A1 | 11/2021 | Suhr et al. |

FOREIGN PATENT DOCUMENTS

| | | |
|---|---|---|
| DE | 3308361 | 9/1984 |
| EP | 0137367 | 11/1989 |
| EP | 0518907 | 12/1992 |
| EP | 0424801 | 11/1993 |
| EP | 0904688 | 3/1999 |
| GB | 2123959 | 6/1983 |
| WO | 2001035728 | 5/2001 |
| WO | 03098192 | 11/2003 |
| WO | 2008156413 | 12/2008 |
| WO | 2012168528 | 12/2012 |
| WO | WO-2019034443 A1 * | 2/2019 ................ A01J 5/01 |

OTHER PUBLICATIONS

International Preliminary Report on Patentability issued in PCT/NZ2023/050018 on Nov. 7, 2013.
AU2022900361 International-Type Search Report from IP Australia dated Mar. 22, 2022.
AU2022902243 International-Type Search Report from IP Australia dated Sep. 12, 2022.

* cited by examiner

IN-LINE SENSOR, MILKING CLUSTER AND ASSOCIATED METHODS

TECHNICAL FIELD

Described herein is an in-line sensor, milking cluster and associated methods. More specifically, an in-line sensor is described for sensing properties of a pulsed milk flow on a continuous basis. A milking cluster comprising multiple in-line sensors is also described. Methods of use of the in-line sensor and milking cluster to sense properties of the milk flow are also described.

BACKGROUND ART

In-line sensors are used to measure the properties of a liquid. Pulsed milk flows present a challenge to accurate liquid property measurement since the sensors used read very differently when the sensor measures a liquid as opposed and an air or gas spacing between liquid pulses. Ideally, liquid sensors continuously measure liquid properties to ensure a stable sensed reading and not a wildly variable reading as might be the case in a pulsed flow scenario. Existing in-line sensors for measuring pulsed milk flows can include trap type systems, wells and the like that act to hold some of the pulsed liquid stream from which a measurement may be taken.

In-line sensing of pulsed liquid properties may be used in a wide variety of applications such as in food production, beverage production, chemical processing, petrochemical refining, water processing and distribution and so on. The pulse may be generated by the pump or vacuum systems used to draw liquid down a tube. By way of demonstration hereafter, diary processing and measurement of a milk liquid stream is described however, this should not be seen as limiting.

In a dairy milking environment, particularly for dairy cows but also for other lactating farmed animals such as sheep and goats, sophisticated milking system already exist, sometimes with elaborate sensing and measurement apparatus. Despite existing system complexity and development, detecting animal health and in particular, mastitis infection, remains a challenging area. Bovine mastitis is the most widespread and costly disease in the dairy industry. Mastitis reduces milk yield, and is poor for animal health leading to pain, swelling, fever and in worst cases, animal death.

Clinical bovine mastitis is inflammation of the udder, usually due to bacterial infection. Bovine mastitis can also exist in a sub-clinical state with no physical symptoms. Both clinical and sub-clinical mastitis cause an elevated somatic cell count and conductivity in milk collected from the animal and hence existing on-farm methods of detecting mastitis are usually completed through measurement of somatic cell count or conductivity in the milk. Other proxies for mastitis include higher milk temperature and lower milk yield. Elevated somatic cell counts are a negative metric for milk quality and can lead to rejection of milk and hence loss in production and profits.

Detecting mastitis (clinical or sub-clinical) is important as early detection reduces infection spread and improves treatment outcomes. Early detection both in timing and as close to an individual animal or teat may be also be highly useful as this may avoid downgrade or contamination of an entire batch of milk and may help to quickly identify which animal or even teat is infected. Existing detection options for farmers are either through manual testing of milk collected, manual testing of milk from a particular teat or udder mixture or via automated sensors. Existing automated sensors in the art however tend to be expensive to purchase, only measure downstream mixtures of milk, complex to operate and require difficult integration. Art sensors can also be a poor option for food/beverage environments since they do not drain or only poorly drain and hence they may harbour microbes or retain clean in place (CIP) chemicals that could contaminate the wider liquid stream processed.

Some attempts have been made to produce in-line sensors for mastitis detection such as those described in at least EP0137367A1, US2021/0239671, US2021/0360891, WO2012/168528 and EP0904688A1.

The device described in EP0137367 has limitations in that the outlet for milk to exit is a small hole that is elevated relative to the bypass passage hence liquid would always remain in the bypass once a milk flow stopped leading to issues with cleaning. The device is not self-emptying.

US2021/0239671 has sensors that impede the measured liquid passage that would retain some liquid in the measurement channel behind the sensors and which would cause foaming, a further problem that can confound accurate measurements.

US2021/0360891 is similar to US2021/0239671 above in that it is a relatively bulky device that relies on gravity to capture a side flow sample of milk. The main and captured flows of milk are subjected to changes in flow direction that can lead to foaming and turbulence. This change in direction of the sampled milk may mean that trace components only present in a foremilk portion (described further below) become mixed with the wider flow of milk prior to sensing and hence are not detected or become difficult to detect. Complete self-emptying from this device is also unlikely as it is horizontally installed and gravity cannot assist in emptying all of the captured milk from the sensor measuring section leading to potential microbial growth regions in the sensor.

WO2012/168528 has a shut off valve impeding flow of liquid from the measurement cavity that is on the same plane as liquid in the measurement cavity and hence would inherently not self-drain or not entirely self-drain.

EP0904688A1 has a flat face first flange that milk being measured must pass over and through outlet openings. If the device is installed upright as described, inherently, some milk would remain on the flange face. If the device were installed on an angle, significant milk could pool on the lower side of the flange face. The device is not self-emptying.

All of the above devices would not be suitable to install between a milking cup and claw. This is because the weight or geometry or the devices would interfere with surrounding operations and parts. This is thought by the inventor's to be a key reason why sensor technology like this has not been adopted for individual teat milk measurement. Instead, prior art sensors like the above are installed post claw mixing or post mixing of milk from multiple claws/animals. Sensing after mixing is not ideal as errant results may not be traceable to a specific animal (if measuring milk from multiple animals or, may not be traceable to a specific animal teat hence not assist with animal treatment. Also, once multiple flows are mixed, it is not possible to 'un-mix' these flows therefore, contamination by mastitis infected milk may result in considerable volumes of reject milk. Sensing an errant result immediately after the teat may allow reject milk (even from one teat) to be acted on quickly and minimise the likelihood of significant waste or reject milk. Rapid sensing of mastitis infection may also allow for earlier medical intervention to treat the animal.

In addition, milk flows in the above sensors may be convoluted and not measure a foremilk portion (defined further below) of a milk flow. By way of example, EP0137367 forces the measured liquid around the main flow; US2021/0239671 takes water from the side of a main stream which drops into a lower measurement chamber; WO2012/168528 has a wall to deliberately separate the liquid stream into two parts; EP0904688A1 has a lateral passage. These methods would cause foaming and confound the results. The devices described sometimes even cater for foaming in their designs leading to larger volume designs that would inherently lead to larger vacuum pumps and associated apparatus and higher running costs.

As may be appreciated, it may be useful to provide an in-line sensor that is simple to integrate into existing liquid lines; an in-line sensor that is inexpensive and has no or low maintenance requirements; and which ideally is reliable and accurate; or at least provide the public with a choice.

Further aspects and advantages of the in-line sensor, milking cluster and associated methods will become apparent from the ensuing description that is given by way of example only.

SUMMARY

Described herein is an in-line sensor is described for sensing properties of a pulsed milk flow on a continuous basis. A milking cluster comprising multiple pulsed milk flow inputs from lactating animal teats and a mixing point or claw for the multiple inputs is described that includes multiple in-line sensors for each pulsed milk flow input. Methods of use of the in-line sensor and milking cluster are also described.

In a first aspect, there is provided an in-line sensor configured to measure a sensed property of milk collected from a lactating animal, the in-line sensor comprising:
  an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and
  a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;
  wherein the liquid diverter comprises:
    a liquid receiver inlet that receives the secondary flow of milk therein;
    a sensor measuring a property of the secondary flow of milk received in the liquid receiver inlet;
    a flow restrictor outlet configured to restrict a flow rate of the secondary flow of milk from the liquid diverter; and
  wherein the liquid diverter is configured to:
    in use, be aligned so that the liquid receiver inlet is positioned generally above the flow restrictor outlet;
    retain secondary flow of milk about the sensor between pulses of the pulsed milk flow to the in-line sensor; and
    when the pulsed milk flow ceases through the in-line sensor, secondary flow of milk retained about the sensor, self-empties and drains fully via gravity from the liquid diverter via the flow restrictor outlet.

In a second aspect, there is provided a milking cluster for pulsed milk flow collection comprising:
  two or more milking cups and a claw, the two or more milking cups each configured to connect to and directing pulsed milk flows from each of the two or more milking cups to the claw, the claw configured to receive and mix the pulsed milk flows; and,
  intermediate each milking cup and the claw is located an in-line sensor substantially as described above, each in-line sensor configured to sense a characteristic of the pulsed milk flow from an individual milking cup prior to mixing of the pulsed milk flow in the claw.

In a third aspect, there is provided a method of sensing a property of a pulsed milk flow by:
  providing a pulsed milk flow from a milking cup to an in-line sensor substantially as described above; and
  passing the pulsed milk flow through the in-line sensor and receiving sensed characteristics of the pulsed milk flow from the in-line sensor.

In a fourth aspect, there is provided a method of sensing a characteristic of a single teat pulsed milk flow in a milking cluster prior to mixing of multiple pulsed milk flows from multiple teats by:
  installing, intermediate each milking cup and claw in the milking cluster, an in-line sensor substantially as described above;
  providing multiple pulsed milk flows from each milking cup to each in-line sensor; and
  passing the multiple pulsed milk flows through each in-line sensor and receiving sensed characteristics of each pulsed milk flow in each in-line sensor.

In a fifth aspect, there is provided an in-line sensor configured to measure the presence of mastitis infection in a lactating animal, the in-line sensor comprising:
  an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and
  liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;
  wherein the liquid diverter comprises:
    a liquid receiver inlet that receives the secondary flow of milk therein;
    a sensor measuring a conductivity of the secondary flow of milk received in the liquid receiver inlet;

a flow restrictor outlet configured to restrict a flow rate of the secondary flow of milk from the liquid diverter; and wherein the liquid diverter is configured to:
in use, be aligned so that the liquid receiver inlet is positioned generally above the flow restrictor outlet;
retain secondary flow of milk about the sensor between pulses of the pulsed milk flow to the in-line sensor; and
when the pulsed milk flow ceases through the in-line sensor, secondary flow of milk retained about the sensor, self-empties and drains fully via gravity from the liquid diverter via the flow restrictor outlet.

The above described in-line sensor, milking cluster and associated methods may provide a number of benefits over the art such as ease of integration, reliability, low cost, self-cleaning/self-emptying. The in-line sensor may be well suited to food/milk processing applications and the in-line sensor in the inventor's experience is very accurate and reliable. These advantages and others are described further in the detailed description below.

BRIEF DESCRIPTION OF THE DRAWINGS

Further aspects of the in-line sensor, milking cluster and associated methods will become apparent from the following description that is given by way of example and with reference to the accompanying drawings in which:

FIG. 22 illustrates the range of working angles that the in-line sensor may be used in.

DETAILED DESCRIPTION

Figure 1:
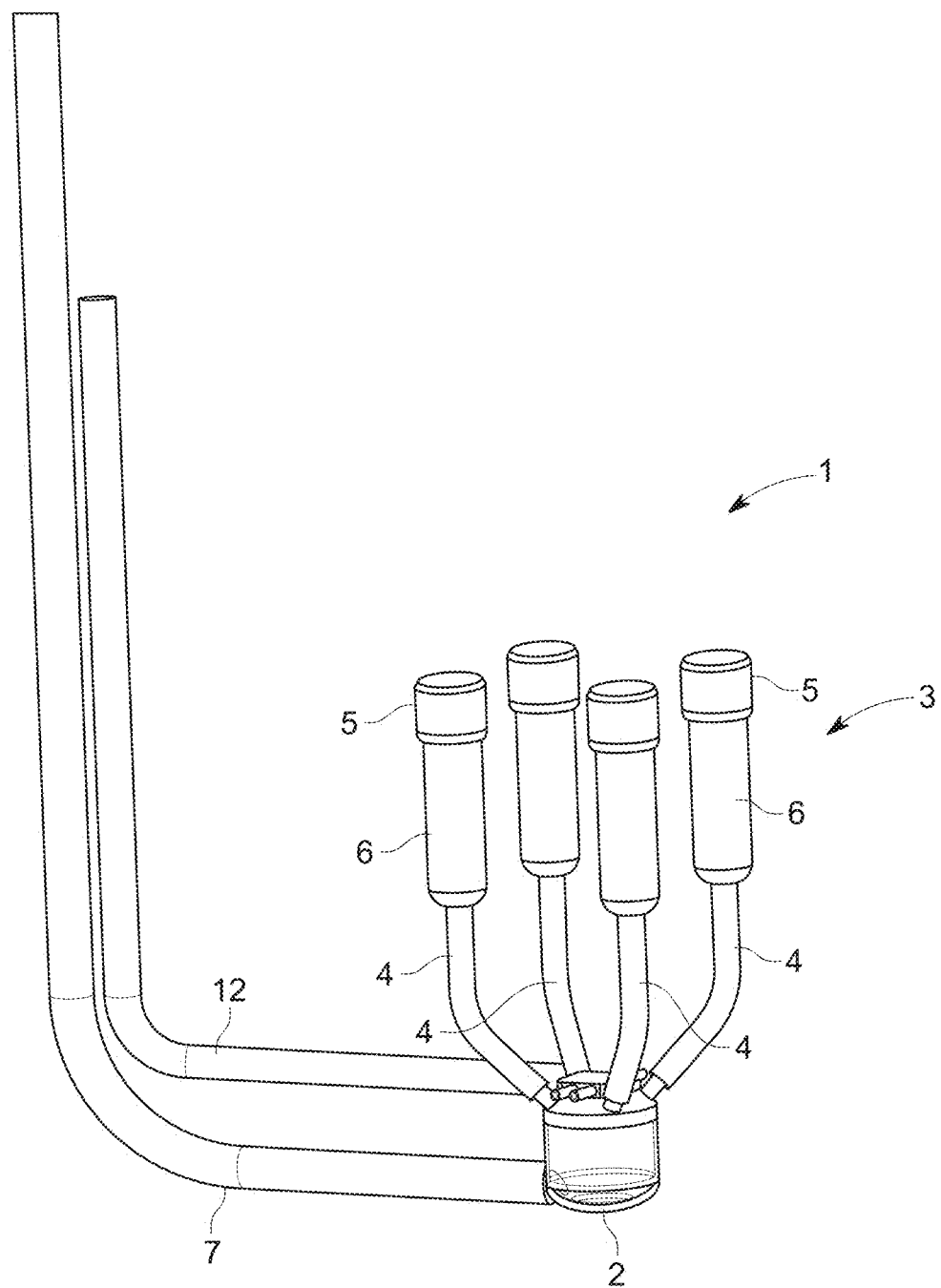
FIG. 1 illustrates a schematic perspective view of a prior art standard milking cluster set-up.

As noted above, described in-line sensor, milking cluster and associated methods provide a number of benefits over the art such as ease of integration, reliability, low cost, self-cleaning/self-emptying.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'pulsed milk flow' and grammatical variations thereof refers to a milk flow that is not continuous in nature and is characterised by breaks in the flow or flow rate, typically with air or gas intervals or gaps between each slug of liquid and/or foaming or other non-liquid matter.

In-Line Sensor

In a first aspect, there is provided an in-line sensor configured to measure a sensed property of milk collected from a lactating animal, the in-line sensor comprising:

an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;

wherein the liquid diverter comprises:
  a liquid receiver inlet that receives the secondary flow of milk therein;
  a sensor measuring a property of the secondary flow of milk received in the liquid receiver inlet;
  a flow restrictor outlet configured to restrict a flow rate of the secondary flow of milk from the liquid diverter; and
wherein the liquid diverter is configured to:
  in use, be aligned so that the liquid receiver inlet is positioned generally above the flow restrictor outlet;
  retain secondary flow of milk about the sensor between pulses of the pulsed milk flow to the in-line sensor; and
  when the pulsed milk flow ceases through the in-line sensor, secondary flow of milk retained about the sensor, self-empties and drains fully via gravity from the liquid diverter via the flow restrictor outlet.

In-Line

The in-line sensor may be located intermediate:
a site for milk collection from a lactating animal; and
a site for collection of milk.
The in-line sensor may be located in a milking cluster intermediate a teat and a storage vat. Alternatively the in-line sensor may be located in a milking cluster intermediate a teat and a spider collection chamber.
The in-line sensor may be located intermediate a pulsed milk flow source and a final collection point for the collected milk.

Elongated Housing

The elongated housing may be an enclosure that directs the pulsed milk flow from the housing inlet to the housing outlet. The elongated housing may be tubular and elongated with the housing inlet and housing outlet at each elongated housing end.

As noted above, the elongated housing may be continuous and straight and may direct the pulsed milk flow from the inlet to the outlet. The elongated housing may have a cylindrical flat internal bore or opening that the liquid diverter is located within.

The elongated housing may define a first internal volume for milk flow therethrough, and a milk flow line absent of the in-line sensor between the milking cup and claw may define a second internal volume for milk flow therethrough. When the in-line sensor is fitted to the milk flow line between the milking cup and claw, the first internal volume may be substantially identical to the second internal volume.

The milk flow line may be a flexible tube, for example a rubber tube. Post fitting of the in-line sensor, the flexible tube may extend:
  from the milking cup to the inlet of the elongated housing of the in-line sensor; or
  from the outlet of the elongated housing of the in-line sensor to the claw; or
  from both the milking cup to the inlet of the elongated housing of the in-line sensor and, as a separate flexible tube, from the outlet of the elongated housing of the in-line sensor to the claw.

In one example, the first internal volume may be less then +/−15% different to the second internal volume.

The elongated housing may define an internal length, width or diameter and volume for milk flow therethrough. Where the in-line sensor is fitted to an existing milk flow line, the enclosure internal length, width or diameter and volume for milk flow may be approximately the same as the removed section of line to which the in-line sensor is fitted. For the purposes of this specification, the term 'approximately' in this context refers to the change in volume with the addition of the in-line sensor being within +/−15, or 10, or 5% of the original volume of the existing line. That is, the in-line sensor is a very compact shape and form. The compact shape and form means that the volume is barely altered and existing infrastructure such as tubes, pumps and wider apparatus operation may remain unchanged. As may be appreciated, art in-line sensors that alter the volume and impede milk through therethrough may present milking cup handling issues. The added bulk in size from sensors is problematic since there is already limited space under the cow's udder in a milking parlour. Milking cups that are longer end up resting on the concrete platform for example which is undesirable. Greater width milking cups obstruct cup fitting and removal. Other issues around added sensor bulk also exist such as possible higher vacuum input and potentially higher running costs or even new equipment such as higher powered vacuum pumps.

The elongated housing at the housing inlet and/or housing outlet may mate with a pulsed milk flow tube or pipe or other pulsed milk flow directing means. Mating may be via a barbed fitting with or without a hose clamp to lock the tube to the housing inlet or housing outlet.

Pulsed Milk Flow

The pulsed milk flow as noted above is a pulsed flow. Pulsing may also be defined as being an intermittent flow. Pulsing may result in gaps in milk flow within the in-line sensor elongated housing such as by gaps in milk delivery, presence of foam or air gaps in the milk flow or incomplete filling of the elongated housing (not a continuous flow).

Pulsed milk flow may be generated by a pulsating pump. The pulsating pump may be: a diaphragm pump, a positive displacement pump or a peristaltic pump.

As may be appreciated, in a pulsed milk flow, where a sensor does not have a liquid diverter like that described, the sensed properties measured may fluctuate considerably between pulses and, hence not give an accurate result for the sensed milk property. The liquid diverter as used in conjunction with the in-line sensor described provides significant advantages in that the milk measurement is continuous and not fluctuating as a sample of milk in the second flow of milk is always present about the sensor(s).

Flow

The term 'flow' as used herein refers to movement of milk in substantially liquid form from one point to another point. In the context of the elongated housing, each pulse of milk moves from the housing inlet to the housing outlet. This may via the elongated housing primary flow of milk or, as a secondary flow of milk via the liquid diverter, past the sensor and out of the flow restrictor back into the primary flow of milk.

The primary flow of milk through the elongated housing and the secondary flow of milk through the liquid diverter, may flow in a coaxial direction along a longitudinal axis of the elongated housing. Flow by the primary flow of milk may be unimpeded through the elongated housing. The primary and secondary milk flows may be offset from each other in a direction orthogonal to the longitudinal axis of the primary flow of milk and the secondary flow of milk. The longitudinal axis of the primary flow of milk and the secondary flow of milk may common with the longitudinal axis of the elongated housing from the housing inlet to the housing outlet.

As noted above, the flow of milk through the elongated housing and liquid diverter (primary and secondary flows) may be coaxial along a longitudinal axis of the in-line sensor albeit that the primary and secondary flows of milk may be offset from each other.

Foaming

The elongated housing may be configured to minimise foaming or aeration of the pulsed milk flow therethrough. Minimisation of foaming or aeration may be achieved in the inventor's experience by interfering with a minority of the pulsed milk flow through the elongated housing. The majority or substantially all of the pulsed milk flow may flow as a primary flow of milk through the elongated housing without being diverted in flow direction.

As may be appreciated, foaming or aeration of milk is a design challenge particularly where accurate sensing is required. A sensor configured to measure a milk property when placed into a foam will either not sense a reading at all or, will sense an incorrect reading since, for example, air/foam has a very different conductivity to a liquid. As noted, the in-line sensor described may be configured to minimise foaming or aeration of a pulsed milk flow therethrough by design features such as a uniform flow direction, minimising disruption of flow direction, measurement in the same flow direction and so on. Art in-line sensors may be designed to siphon of a sample side stream that is directed away from the main milk flow and as a result, foaming can become an issue that art designs are even designed to cater for. In this case, no special catering is made for foaming since, in the inventor's experience, no foaming occurs, or at least no foaming occurs that impacts on sensor measurements made in the liquid diverter.

Quantity Primary and Secondary Flows of Milk

The majority of each pulse of the pulsed milk flow may move directly through the elongated housing as a primary flow of milk and does not pass or is not captured in the liquid diverter as the secondary flow of milk. Greater than 60, or 70, or 80, or 90, or 95% by volume of each pulse of the pulsed milk flow moves directly through the elongated housing as a primary flow of milk and is not captured in the liquid diverter as a secondary flow of milk. Conversely, less than 40, or 30, or 20, or 10, or 5% by volume of each pulse of the pulsed milk flow is captured as the secondary flow of milk in the liquid diverter.

Flow Rate

Secondary flow of milk passing through the liquid diverter may move at a relatively slower flow rate than the primary flow of milk flow rate through the elongated housing i.e. the time taken to travel (residence time) between the housing inlet to the housing outlet for the secondary flow of milk is longer than the time taken for the primary flow of milk.

The liquid diverter may be configured to have a residence time for secondary flow of milk retained in the liquid receiver so as to slow emptying of the liquid diverter. The secondary flow of milk residence time in the liquid diverter may vary from 0.1 second to 1 minute, although there may be some variation in this residence time for a smaller portion (e.g. less than 20, or 15, or 10, or 5%) of the secondary flow of milk.

Foremilk

The primary flow of milk may also be separated into a foremilk portion and a main flow. The term 'foremilk' as used herein refers to the initial 'slug' of milk that passes through the in-line sensor from each pulse of pulsed milk flow.

The in-line sensor may be configured to capture and measure characteristics of a foremilk portion of each pulse of the pulsed milk flow passing through the in-line sensor.

The foremilk or forward most portion of a slug of milk that enters the in-line sensor may be where unusual milk properties such as elevated somatic cells from a mastitis infection may be at a highest concentration. The inherent turbulence of the latter part of the slug of milk pulse may homogenise any anomalies in the milk pulse of slug. As a result, it may be an advantage to preferentially separate the foremilk portion of one or all of the milk pulses that pass through the in-line sensor.

Liquid Diverter Location in the Elongated Housing

The liquid diverter may, as noted elsewhere, be in-line and coaxial with the pulsed milk flow through the in-line sensor elongated housing.

The liquid diverter may be offset to one side of the elongated housing so as to be offset relative to a primary flow of pulsed milk flow through the elongated housing.

It is the inventor's experience that this design successfully captures the foremilk of each slug of milk in a repeatable and reliable manner. This leads to better sensed readings of anomalies in the milk. Art in-line sensors that disrupt the flow of milk may cause turbulence and/or not capture foremilk preferentially hence, may miss small changes in concentration of sensed variables present in the foremilk.

Liquid Diverter/Liquid Receiver

As noted above, the liquid diverter comprises:
a liquid receiver inlet that receives the secondary flow of milk therein;
a sensor measuring a property of the secondary flow of milk received in the liquid receiver inlet; and,
a flow restrictor outlet configured to restrict a flow rate of the secondary flow of milk from the liquid diverter.

The liquid diverter may be configured to split the pulsed milk flow into a primary flow of milk and a diverted secondary flow of milk. The liquid diverter may be configured so that primary and secondary flows of milk are coaxial i.e. in the same flow axis albeit one flow axis is offset from the other. The coaxial flow may be coaxial with the longitudinal axis of the in-line sensor elongated housing.

The flow restrictor outlet may not be so small as to stop all secondary flow of milk from the liquid diverter. It is essential however that, when a pulsed milk flow into the in-line sensor halts, any secondary flow of milk in the liquid diverter self-empties and drains fully to leave the liquid diverter empty of secondary flow of milk.

The liquid diverter may be located on one side of the elongated housing as noted above and hence interferes with only a small portion of the volume of the foremilk of a pulsed milk flow through the in-line sensor. The liquid diverter may be defined partly by a wall of the elongated housing itself and partly by a second wall section, the second wall section located inside the elongated housing so as to segregate off a portion of the elongated housing through which secondary milk flow passes. In cross-section, about the location of the liquid diverter, the elongated housing may be defined by a larger opening on an upstream side along with a smaller opening also on the upstream side located within the larger opening. The liquid diverter upstream opening in cross-section may be co-axial with the longitudinal axis of the elongated housing. The liquid diverter central longitudinal axis may however be offset relative to the central longitudinal axis of the elongated housing, for example, off-set to one side of the elongated housing. The liquid diverter second wall section may be a flat wall shape or rounded or polygonal. The exact shape used may be to suit ease of moulding and may not be critical to the nature of the flow and flow diversion.

Flow Restrictor

The flow restrictor may be a narrowed outlet from the liquid diverter that slows the rate of flow of secondary flow of milk from the liquid diverter.

The narrowed outlet may taper in size/diameter from a wider diameter to a narrow diameter. Tapering may be by reducing the flow restrictor diameter assuming the flow restrictor is conical in shape. Other shapes are possible as well.

The final size of the flow restrictor may vary depending on the nature of the milk stream and degree of residence time desired.

Pulsed or Uneven Liquid Stream Flow

As noted elsewhere in this specification, the pulsed milk flow to the in-line sensor may be un-even or pulsed with gaps in flow yet, the in-line sensor is configured to always provide milk to the sensor to allow for even and continuous milk property measurement. As may be appreciated, pulsed or un-even flows may result in air gaps that may cause sensed measurements to become unstable, vary significantly between liquid and air gaps, or simply give false readings. The in-line sensor described avoids this by continuously always retaining at least some milk from each pulsed milk flow between pulses or un-even flow where a sensed measurement takes place. The liquid diverter may also preferentially capture the foremilk of a slug of milk as described in detail above. This may lead to measurement of possible elevated concentrations, typically present in the foremilk and less so in the subsequent milk flow. As described however, once the residence time of the liquid diverter is reached (timed with when a pulsed milk flow fully stops to the in-line sensor), the liquid diverter fully drains.

The liquid diverter may be configured so that the rate of draining of secondary milk flow from the liquid diverter ensures that the secondary milk flow always has at least some milk from each pulse of pulsed milk flow passing through the in-line sensor. Expressed another way, the secondary milk flow drains at a sufficient rate to always leave at least some gap for a next pulse of milk to fill. By designing the emptying rate in this manner, secondary flow of milk in the liquid diverter does not become stagnant with one pulse of milk sample and is constantly refreshed as pulses of pulsed milk flow move past the liquid diverter ensuring that any changes in milk properties are rapidly sensed.

Materials Used

The elongated housing and liquid diverter may be a single piece mould that a sensor is attached to.

As noted, the in-line sensor, except the sensor itself, may be a single piece mould that a sensor is attached to. The liquid diverter detail described above may be integral to the single piece mould as well. Further, the in-line sensor may be entirely passive and may have no moving parts. Sensing occurs passively and mixing, movement of sample, removal of sample is not required.

The in-line sensor may be formed as a single shaped item, with the exception that any sensors used are fitted after manufacture of the in-line sensor. The sensor(s) e.g. probes, may be inserted into the in-line sensor and held in place through friction, adhesive or fastener(s).

The mould may be manufactured from polymers or metals. Where food safety is an issue, the in-line sensor may be made from a food safe plastic or stainless steel. In other applications, it may be appropriate to use other types of materials for the in-line sensor to reflect the pulsed liquid stream properties and importance around fouling/cleaning and part longevity.

Liquid Diverter Position/Flow Diverting Mechanism

As noted above, in use, the liquid diverter may be aligned so that the liquid receiver inlet is positioned generally above the flow restrictor outlet; the liquid diverter retains secondary flow of milk about the sensor between pulses of the pulsed milk flow to the in-line sensor; and, when the pulsed milk flow ceases through the in-line sensor, secondary flow of milk retained about the sensor, self-empties and drains fully via gravity from the liquid diverter via the flow restrictor outlet.

The elongated housing may be located at an angle relative to a horizontal plane and the liquid diverter may be positioned within the elongated housing to be on a lower side of the in-line sensor. The liquid diverter, in use, may be positioned at a low side or downwards side of the in-line sensor i.e. to use gravity to urge the pulsed milk flow at least partly flow through the liquid diverter. In this example, if the liquid diverter were at an elevated position relative to the pulsed milk flow through the elongated housing, it may be possible for the liquid diverter to not fill and empty in a continuous manner.

In the inventor's experience, the liquid diverter need not be directly below the pulsed milk flow through the in-line sensor and the liquid diverter may be angled relative to a horizontal plane. The elongated housing, in use, may be angled at 60, or 65, or 70, to 75, to 80, or 85, 90 degrees relative to a horizontal plane or from 60 to 90 degrees relative to a horizontal plane.

Flow Diverting Mechanism

The in-line sensor may further comprise at least one flow diverting mechanism that may urge at least part of the pulsed milk flow towards the liquid diverter. The elongated housing, in use, may be angled at 0 to 90 degrees relative to a horizontal plane where a flow diverting mechanism is used. The liquid diverter in this example, may be located distant to a low side of the elongated housing.

Through use of at least one flow diverting mechanism, the working range of angles for the elongated housing may extend beyond a 60-90 degree angle relative to a horizontal plane i.e. also still operate at angles of 0-60 degrees as well and function as intended with a continuous captured secondary flow of milk in the liquid diverter between pulses of pulsed milk flow and with self-emptying once pulsed milk flow stops.

The in-line sensor flow diverting mechanism that urges pulsed milk flow towards the liquid diverter may for example, comprise a ramp or ramps or a gutter or gutters inside the elongated housing that act to re-direct some or all of the pulsed milk flow as a secondary flow of milk towards the liquid diverter.

Sensor

The sensor may measure characteristics of the pulsed milk flow selected from: conductivity, temperature, presence or absence of chemical or bio-chemical marker(s), liquid colour/optical properties, clarity/turbidity, milk flow rate, and combinations thereof.

The in-line sensor may be configured to sense mastitis in the pulsed milk flow to the in-line sensor by measuring a conductivity of the secondary flow of milk as the secondary flow of milk passes through the liquid diverter and past the sensor.

Milk flow rate may be detected indirectly. Small changes in measured conductivity may be sensed as milk flows through the sensor and liquid diverter. These small changes in conductivity may be used to infer the flow rate of milk through the in-line sensor since the changes and flow rate may have a direct relationship.

Multiple sensors may be used sensing the same or different properties of the milk captured in the liquid diverter. For ease of description herein, a single sensor is described however, reference to the singular does not exclude plural sensors unless otherwise stated.

The sensor may communicate directly with secondary flow of milk received in the liquid receiver inlet. For example, a sensor probe or probes may extend into the secondary milk flow. The sensor may not interfere with or, very minimally interfere with, the secondary flow of milk through the in-line sensor and liquid diverter. The sensor may not slow or hinder self-emptying of milk from the liquid diverter.

The sensed properties of the secondary flow of milk may be communicated to a display. The display may be remote to the in-line sensor. The display may be connected via wire or connected wirelessly to the in-line sensor. The sensed parameters may instead be communicated to a processor. Sensed properties that fall outside an expected sensed value or attribute may trigger an alarm or other notification.

Milking Cluster for Pulsed Milk Flow Collection

In a second aspect, there is provided a milking cluster for pulsed milk flow collection comprising:
two or more milking cups and a claw, the two or more milking cups each configured to connect to and directing pulsed milk flows from each of the two or more milking cups to the claw, the claw configured to receive and mix the pulsed milk flows; and,
intermediate each milking cup and the claw is located an in-line sensor, each in-line sensor configured to sense a characteristic of the pulsed milk flow from an individual milking cup prior to mixing of the pulsed milk flow in the claw; and,
each in-line sensor comprising:
an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and
a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;
wherein the liquid diverter comprises:
a liquid receiver inlet that receives the secondary flow of milk therein;
a sensor measuring a property of the secondary flow of milk received in the liquid receiver inlet;
a flow restrictor outlet configured to restrict a flow rate of the secondary flow of milk from the liquid diverter; and
wherein the liquid diverter is configured to:
in use, be aligned so that the liquid receiver inlet is positioned generally above the flow restrictor outlet;
retain secondary flow of milk about the sensor between pulses of the pulsed milk flow to the in-line sensor; and
when the pulsed milk flow ceases through the in-line sensor, secondary flow of milk retained about the sensor, self-empties and drains fully via gravity from the liquid diverter via the flow restrictor outlet.

In the above embodiment, each in-line sensor may sense a property of each individual pulsed milk flow prior to the pulsed milk flow being mixed in the claw/bowl.

The in-line sensors described may be positioned on each small milk tube between the milking cup and claw/bowl. Positioning may be completed by for example, cutting an existing small milk tube between a milking cup and a claw and inserting the newly formed small milk tube ends into the inlet or outlet of the in-line sensor. The in-line sensor may also be supplied as part of the milking assembly with the milking cup and claw. The in-line sensor may also have small milk tubes already fitted to the inlet and outlet of the in-line sensor and these tubes may be fitted to the milking cup and claw.

The in-line sensor as noted elsewhere may have a barb on the inlet and outlet. The inlet and outlet of the in-line sensor may also have a diameter equal to or slightly greater than the diameter of the small milk tube to cause an interference fit with the small milk tube end. The small milk tube ends (the 'cut ends' if cut in the manner noted above) may be slipped onto the inlet or outlet of the in-line sensor and the barb may then engage the small milk tube ends to prevent reverse disengaging movement of the small milk tube ends from the inlet or outlet of the in-line sensor. The inventor's have found that this slip fit and barb is sufficient to retain the small milk tube ends to the in-line sensor during milking operation. Sleeves or fittings may optionally be used to tighten the small milk tube ends to the in-line sensor if desired.

The above milking cluster has the advantage of sensing and measuring milk properties from an individual teat and from the foremilk of each slug of milk from an individual teat. This then allows identification not only of which lactating animal may be producing milk with a particular sensed property but also which teat may be producing milk with the sensed property.

Method of Sensing

In a third aspect, there is provided a method of sensing a property of a pulsed milk flow by:
providing a pulsed milk flow from a milking cup to an in-line sensor; and
passing the pulsed milk flow through the in-line sensor and receiving sensed characteristics of the pulsed milk flow from the in-line sensor; and
wherein the in-line sensor comprises:
an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;

wherein the liquid diverter comprises:
  a liquid receiver inlet that receives the secondary flow of milk therein;
  a sensor measuring a property of the secondary flow of milk received in the liquid receiver inlet;
  a flow restrictor outlet configured to restrict a flow rate of the secondary flow of milk from the liquid diverter; and wherein the liquid diverter is configured to:
  in use, be aligned so that the liquid receiver inlet is positioned generally above the flow restrictor outlet;
  retain secondary flow of milk about the sensor between pulses of the pulsed milk flow to the in-line sensor; and
  when the pulsed milk flow ceases through the in-line sensor, secondary flow of milk retained about the sensor, self-empties and drains fully via gravity from the liquid diverter via the flow restrictor outlet.

Method of Sensing Multiple Streams

In a fourth aspect, there is provided a method of sensing a characteristic of a single teat pulsed milk flow in a milking cluster prior to mixing of multiple pulsed milk flows from multiple teats by:
  installing, intermediate each milking cup and claw in the milking cluster, an in-line sensor;
  providing multiple pulsed milk flows from each milking cup to each in-line sensor; and
  passing the multiple pulsed milk flows through each in-line sensor and receiving sensed characteristics of each pulsed milk flow in each in-line sensor; and
  wherein each in-line sensor comprises:
    an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and
    a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;
    wherein the liquid diverter comprises:
      a liquid receiver inlet that receives the secondary flow of milk therein;
      a sensor measuring a property of the secondary flow of milk received in the liquid receiver inlet;
      a flow restrictor outlet configured to restrict a flow rate of the secondary flow of milk from the liquid diverter; and
    wherein the liquid diverter is configured to: in use, be aligned so that the liquid receiver inlet is positioned generally above the flow restrictor outlet;
      retain secondary flow of milk about the sensor between pulses of the pulsed milk flow to the in-line sensor; and
      when the pulsed milk flow ceases through the in-line sensor, secondary flow of milk retained about the sensor, self-empties and drains fully via gravity from the liquid diverter via the flow restrictor outlet.

Mastitis Detection In-line Sensor

In a fifth aspect, there is provided an in-line sensor configured to measure the presence of mastitis infection in a lactating animal, the in-line sensor comprising:
  an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with pulsed milk flow through the elongated housing; and
  a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing;
  wherein the liquid diverter comprises:
    a liquid receiver inlet that receives the secondary flow of milk therein;
    a sensor measuring a conductivity of the secondary flow of milk received in the liquid receiver inlet;
    a flow restrictor outlet configured to restrict a flow rate of the secondary flow of milk from the liquid diverter; and
  wherein the liquid diverter is configured to:
    in use, be aligned so that the liquid receiver inlet is positioned generally above the flow restrictor outlet;
    retain secondary flow of milk about the sensor between pulses of the pulsed milk flow to the in-line sensor; and
    when the pulsed milk flow ceases through the in-line sensor, secondary flow of milk retained about the sensor, self-empties and drains fully via gravity from the liquid diverter via the flow restrictor outlet.

In the above aspect, the in-line sensor is configured to sense the presence or otherwise of mastitis infection of a lactating animal via the milk by measuring the milk conductivity. The art teaches that milk conductivity is a useful proxy to indicate the presence of a mastitis infection in a lactating animal, mastitis resulting in an elevated somatic cell count (SCC) in milk produced by the lactating animal. Mastitis infection may elevate SCC and milk conductivity, the latter of which may be sensed using an electrical probe or probes as the sensor(s).

Advantages

The above described in-line sensor, milking cluster and associated methods provide a number of benefits over the art. Examples of advantages may include:

- Ease of integration—the in-line sensor(s) described may easily be integrated as a retrofit or original equipment manufacture (OEM) into art milking cluster. This can be completed with minimal training and minimal skill to complete.
- No existing capital equipment needs to be added or removed thereby removing much of the cost of art in-line sensors.
- The shape of the in-line sensor described is of similar form to an existing teat cup to claw tube to which the in-line sensor is fitted. This helps as may avoid snag points for the tube(s) being caught on other items.
- There are no moving parts to the in-line sensor and the in-line sensor described is entirely passive. Removal of moving parts tends to make designs like this more robust and requiring minimal (if any) maintenance.
- The in-line sensor cost may be so small as to negate the need for on-going maintenance and the in-line sensors may simply be disposed of a replaced on a periodic basis instead of repaired.
- The in-line sensors do not require any special cleaning and the inherent designed for self-emptying means that the in-line sensors are food safe and can be used in milk manufacture and clean in place (CIP) operations necessary for milk collection apparatus.
- Installation and testing of the in-line sensors may be fast and, in the inventor's experience, reliable and accurate. No extra steps are required during milk collection to obtain sensed results as sensing by the in-line sensor may occur continuously and inherently by design as operation occurs. This avoids added processing steps and risk of forgetting to run tests during milk collection.
- In the inventor's experience, accuracy of the sensed results is very high (90, or 95% or greater accuracy). In the case of milking cluster, the ability to sense individual milk flows prior to mixing may be valuable to determine which flow source (teat) the errant result may be occurring from. The combined results of multiple in-line sensors may be of additional benefit to avoid any false positive results. In addition, more than one milk property may be tested at each in-line sensor which may also reduce the frequency of false positive results.
- Cost as noted above for the described in-line sensor maybe low. Installation as noted above is simple. The parts are inexpensive and use of the described in-line sensor may avoid costs associated with on-going labour or changes to other capital items.
- Versatility—the in-line sensor described may be used to sense a variety of pulsed milk flow properties/characteristics.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which the embodiments relate, such known equivalents are deemed to be incorporated herein as if individually set forth.

WORKING EXAMPLES

The above described in-line sensor, milking cluster and associated methods are now described by reference to specific examples referring to bovine milk collection as an application. As noted elsewhere, this should not be seen as limiting since the in-line sensor, milking cluster and associated methods could be used for other lactating animals as well such as sheep and goats. The following item numbers and items are referred to in the Examples below:

1 Cluster
2 Bowl or claw
3 Cups
4 Milk tube
5 Liner
6 Metal shell
7 Tube connection to vat
7A Air line
10 In-line sensor
11 Display
12 Air line
20 Elongated housing
21 Liquid diverter
22 Liquid receiver inlet
23 Sensor
24 Flow restrictor outlet
25 Sensor probes
26 Housing inlet
27 Housing outlet
28 Barb
30 Wall of housing
31 Second wall section
40 Primary flow of milk
41 Secondary flow of milk
50 Flow diverting mechanism
51 Ramp
70 Gutter
100 First pulse of milk
110 First pulse secondary flow of milk
115 First pulse primary flow of milk
120 First pulse foremilk
200 Second pulse of milk
210 Second pulse secondary flow of milk
215 Second pulse primary flow of milk
220 Second pulse foremilk
300 Upper line on graph showing conductivity for a milk sample with no somatic cell count
350 Lower line on graph showing conductivity for a milk sample with elevated somatic cell count
X Low or downwards side of the in-line sensor and elongated housing
YY Angle of in-line sensor relative to a horizontal plane
ZZ Horizontal plane
aa Elongated housing diameter
bb Flow restrictor outlet diameter
CC Liquid diverter diameter

EXAMPLE 1

In this example, the basic form of the in-line sensor is described with reference to the use of the in-line sensor integrated into a milking cluster.

Figure 2:
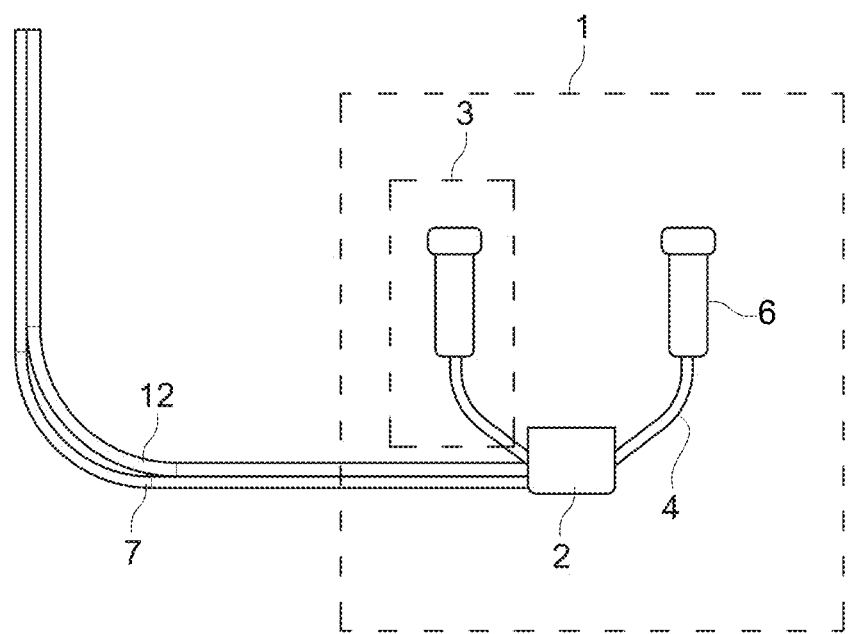
FIG. 2 illustrates a schematic side elevation view of the above prior art standard milking cluster set-up.

FIG. 1 and FIG. 2 show a prior art standard milking cluster set-up. The cluster 1 comprises a bowl/claw 2 which connects to four cups 3 which are made up of a 'liner', the liner being a short milk tube 4, liner 5 and a metal shell 6. The bowl 2 also has a tube connection 7 to the storage vat (not shown). The cups 3 are connected to animal teats (not shown) and a vacuum is provided by an airline (7A) that pulls the milk from the animal udder (not shown) into the bowl 2 in a pulsed manner via a pulsed vacuum pressure to pump the milk intermittently from the animal and then into the vat (not shown) via the tube connection 7.

Figure 3:
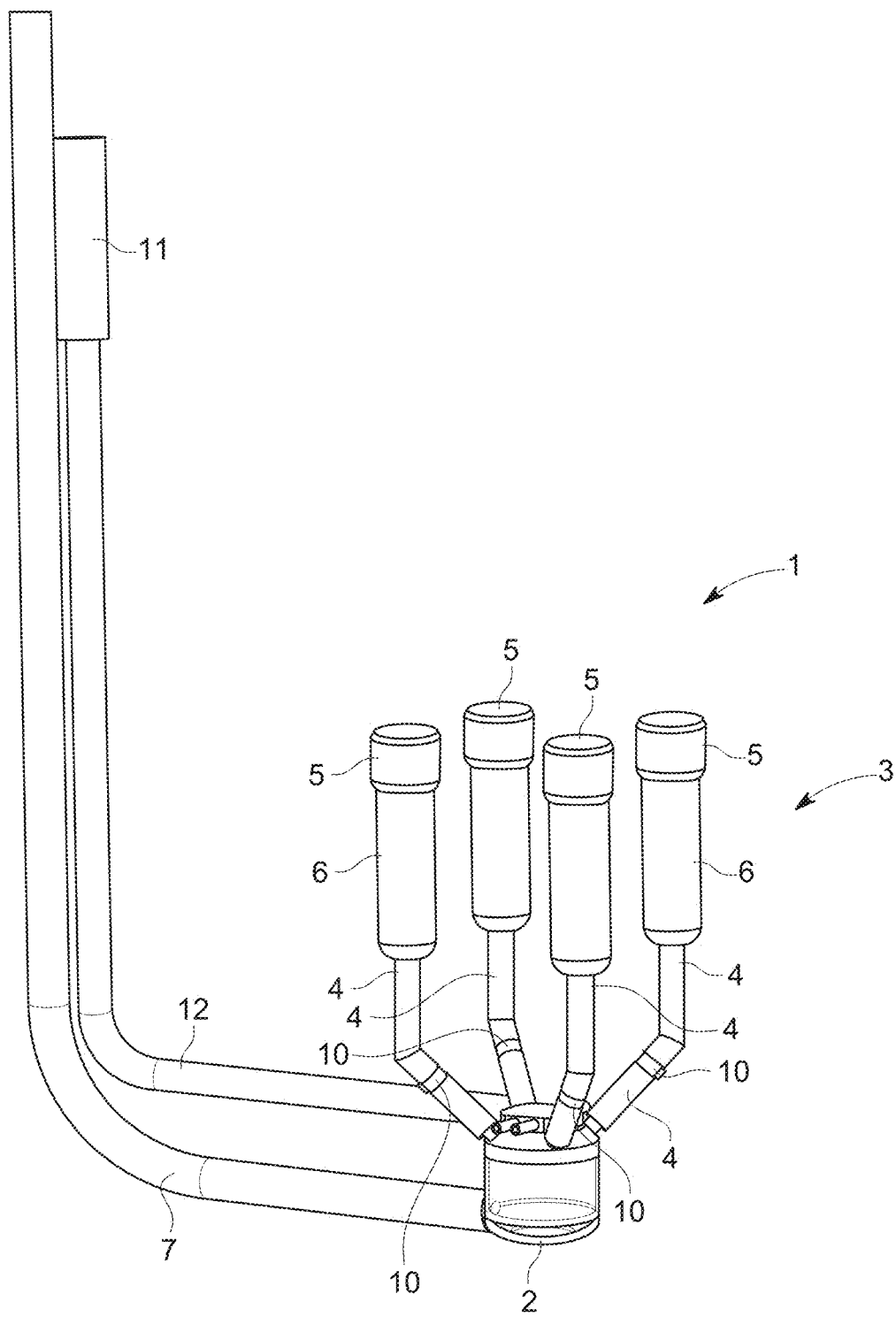
FIG. 3 illustrates a schematic perspective view of a milk cluster with in-line sensors integrated into the milk cluster.
Figure 4:
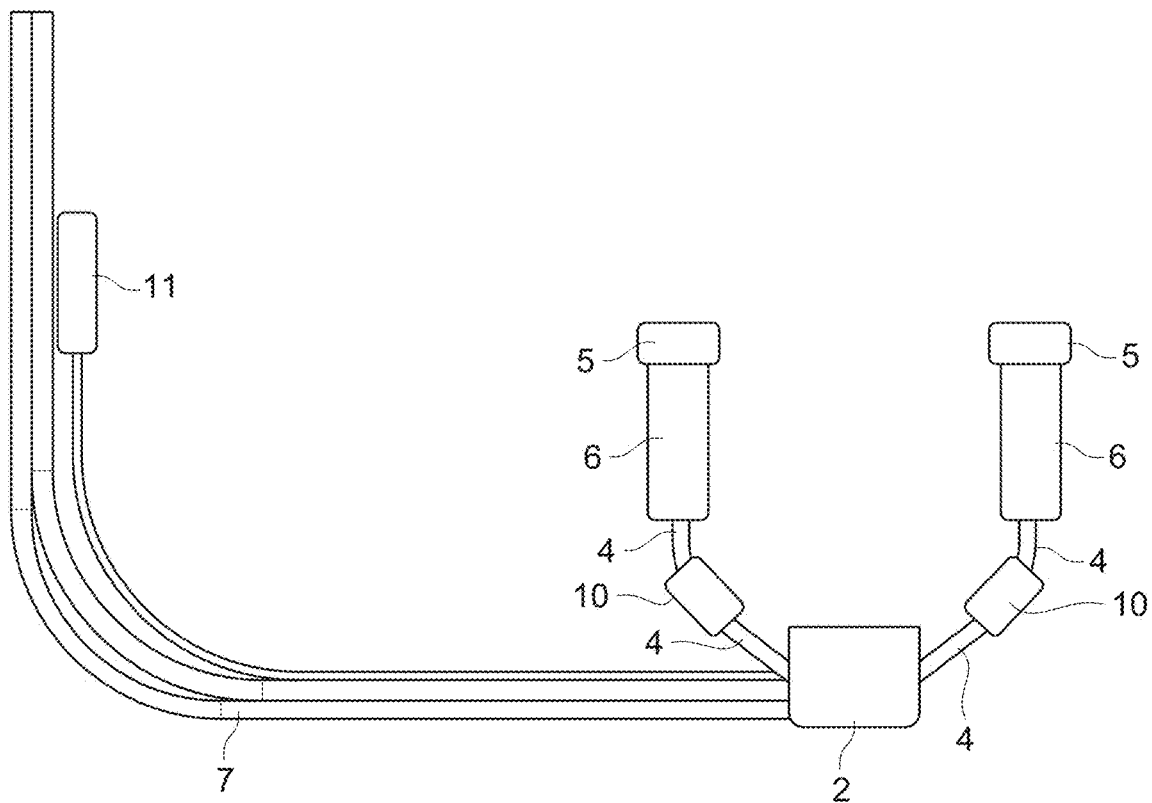
FIG. 4 illustrates a schematic side view of the above embodiment of a milk cluster with in-line sensors integrated into the milk cluster, the in-line sensors shown in an exaggerated large size to indicate their position.

FIG. 3 and FIG. 4 show the cluster 1 set up with in-line sensors 10 integrated into the cluster 1. FIG. 3 shows an accurate representation of the in-line sensor 10 size which as shown is largely integral with the milk flow line being flexible tubes 7 linked between the milking cup 3, in-line sensor 10 and claw 2. The in-line sensor 10 has minimal if any external intrusion and the size and shape of the flexible tube 7 is barely altered (+/−15% by volume change to if no in-line sensor 10 were present). FIG. 4 shows the in-line sensor 10 drawn deliberately larger for the purposes of the schematic and to show the in-line sensor 10 location(s). The cluster 1 in this case comprises four in-line sensors 10 which connect to the short milk tube 4 of each cup 3. The in-line sensors 10 connect via wires (not shown) to a control and display unit (CDU) 11 that may be mounted on the cluster 1 airline 12 and tube connection 7 or any other point convenient to the cluster 1. The in-line sensors 10 in this embodiment measure at least one property of the milk (not shown) collected from each teat/quarter (not shown), and the CDU 11 displays the measured parameter(s). As can be seen, particularly in FIG. 3, the in-line sensors 10 do not change or only minimally change the milk tube 4 length or diameter (and hence volume). No new or altered apparatus may be needed to implement use of the in-line sensors 10 such as upgraded vacuum pumps (not shown). Some art devices substantially increase the volume therefore increasing bulk and weight of the tubes 4 or requiring the introduction of higher powered vacuum pumps to draw a vacuum in the larger volume. The housing outlet 27 discharges the milk from the in-line sensor to the claw/bowl 2.

Figure 5:
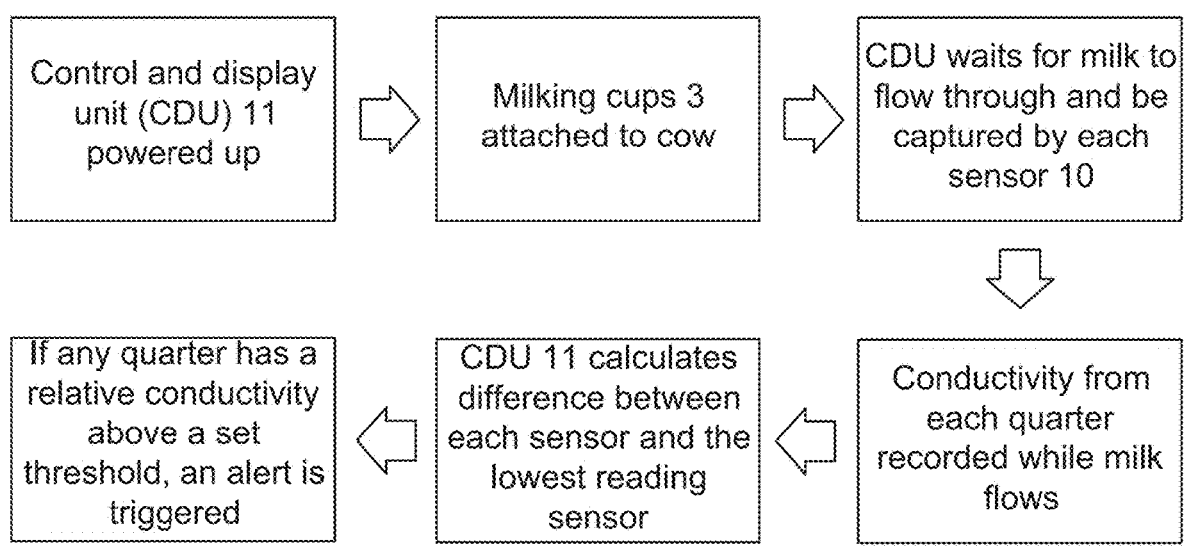
FIG. 5 illustrates a flowsheet for one embodiment of how the milk cluster and in-line sensing arrangement operates.

FIG. 5 illustrates a flowsheet for one embodiment of how the apparatus operates provided by way of example. It should be appreciated that the flowsheet of use may vary, for example, if the CDU is eliminated and the sensed parameters are sent to a remote processor such as a mobile phone or computer (not shown).

EXAMPLE 2

In this example, details of the in-line sensor 10 are described.

Figure 6:
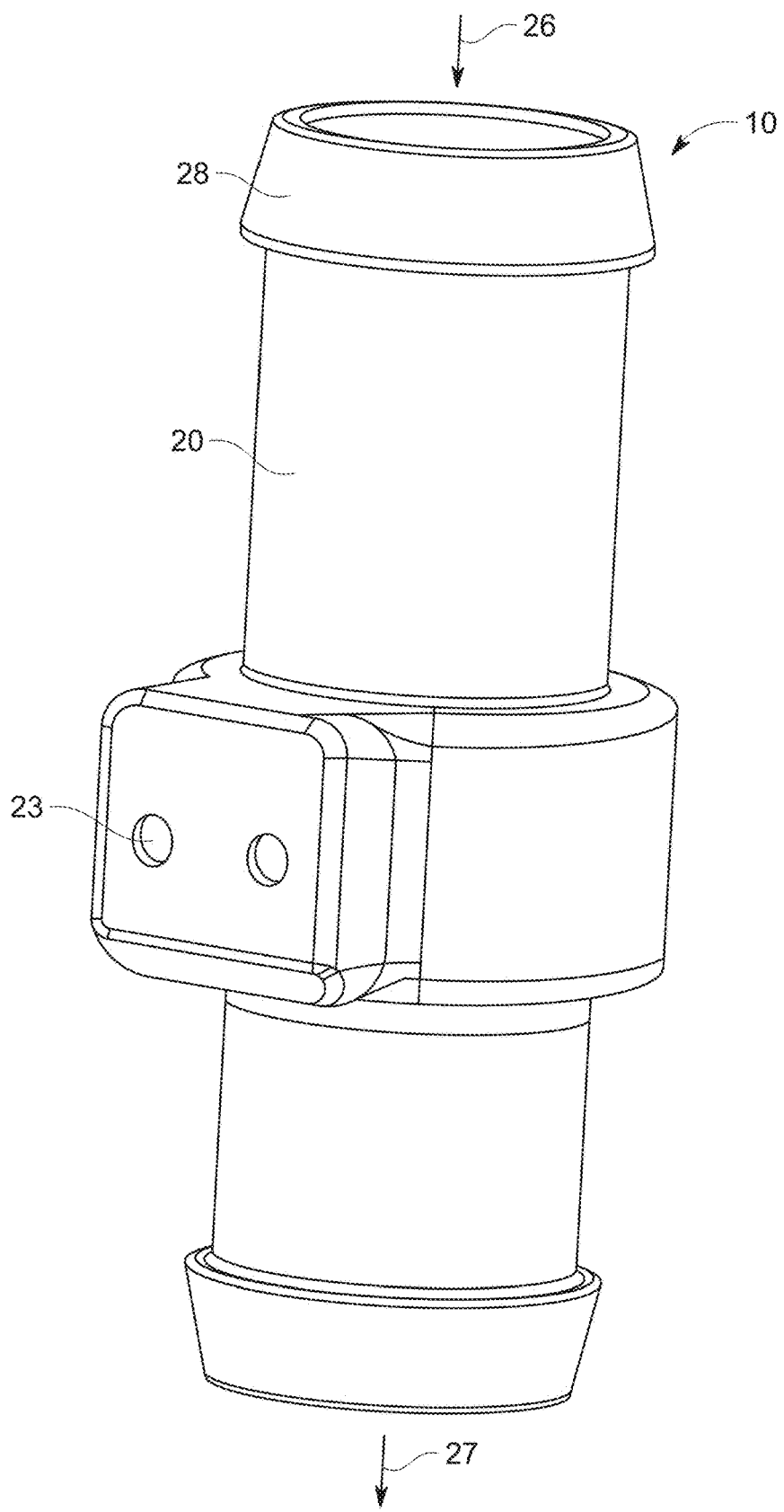
FIG. 6 illustrates a perspective view of the in-line sensor itself.
Figure 7:
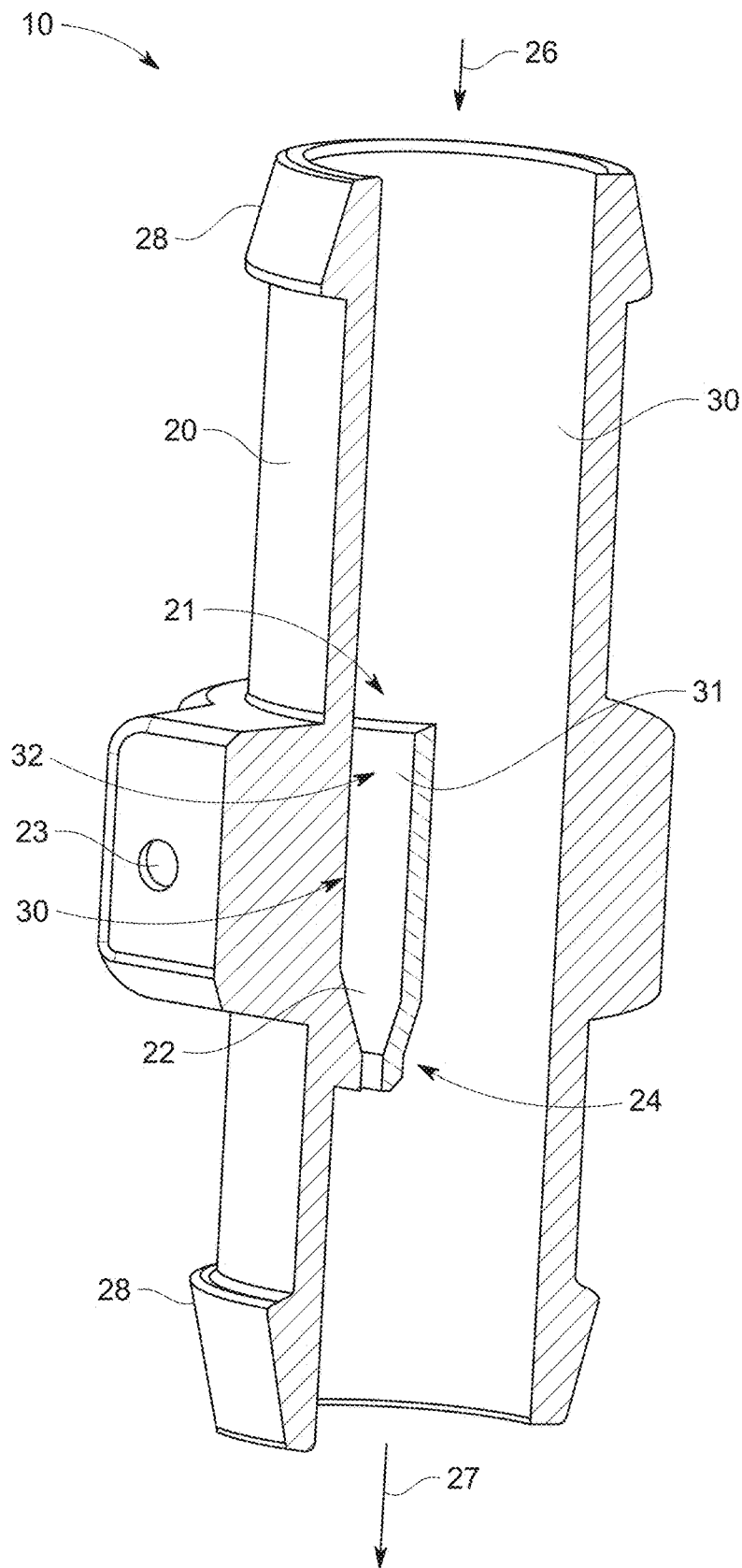
FIG. 7 illustrates the in-line sensor in a cross-section perspective view along the longitudinal vertical axis of the in-line sensor.
Figure 8:
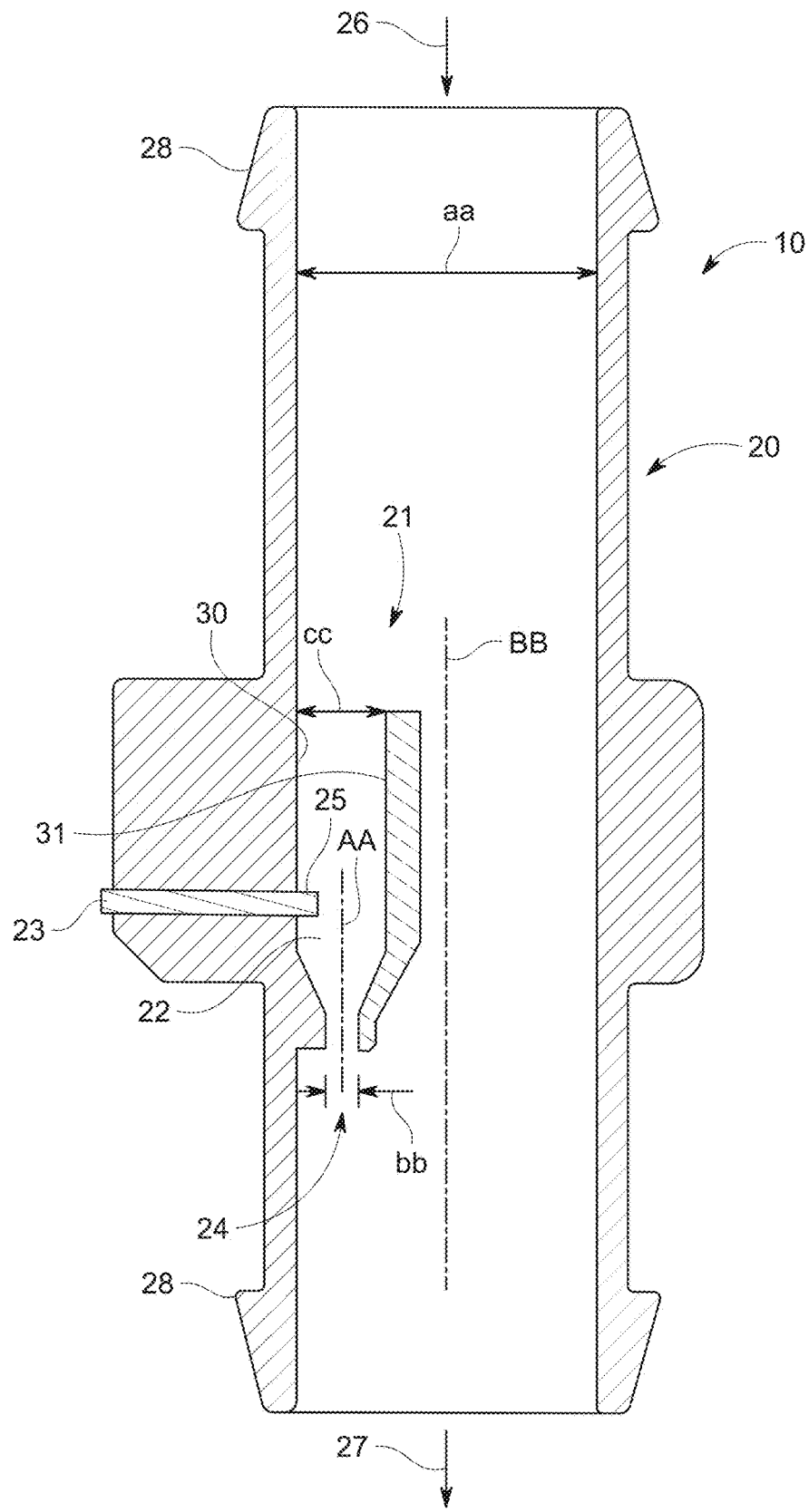
FIG. 8 illustrates a side cross-section view of the in-line sensor.

FIG. 6 illustrates a perspective view of the in-line sensor 10 and FIG. 7 illustrates the in-line sensor 10 in a cross-section perspective view along the longitudinal vertical axis of the in-line sensor 10. FIG. 8 illustrates a side cross-section view of the in-line sensor 10.

As shown, the in-line sensor 10 comprises an elongated housing 20 configured to receive a pulsed milk flow 100, 200 therethrough and a liquid diverter 21 inside the elongated housing 20, the liquid diverter 21 configured to receive part of the pulsed milk flow 100, 200 moving through the elongated housing 20 termed a secondary flow of milk 41 herein, the remainder of the milk being a primary flow of milk 40 that passes directly through the elongated housing 20 and not via the liquid diverter 21.

The liquid diverter 21 comprises a liquid receiver inlet 22, a sensor 23 sensing at least one property of primary flow of milk 40 in the liquid diverter 21; and a flow restrictor outlet 24 configured to restrict flow of secondary flow of milk 41 from the liquid diverter 21. The in-line sensor 10 liquid diverter 21 is configured to self-empty of secondary flow of milk 41 captured when pulsed milk flow 100, 200 ceases through the elongated housing 20.

The in-line sensor 10 may be located intermediate a site for milk collection from a source e.g. a dairy cow (not shown) and a site for collection of milk e.g. the bowl 2 described in Example 1.

The sensor 23 as shown may be a probe or probes 25 that protrude into the liquid receiver 22. The sensor(s) 23 may measure captured liquid properties such as conductivity and other properties noted in the above description. The sensor probe(s) 25 do not impede or hinder self-emptying of secondary flow of milk 41 the liquid diverter 21.

The elongated housing 20 as shown is a straight tubular elongated enclosure that directs a flow of pulsed milk flow 100, 200 from a housing inlet 26 to a housing outlet 27. The elongated housing 20 at the inlet 26 and/or outlet 27 has a barb 28 to mate with a pulsed milk flow tube (not shown). The elongated housing 20 in this example provides a directing means for a primary flow of milk 40 from the housing inlet 26 to the housing outlet 27. As can be seen in the drawings, the in-line sensor 10 elongated housing 20 is of similar form to a milk tube 4 to which it is fitted which may be helpful for usability.

The liquid diverter 21 has a form that provides a secondary smaller chamber area. The liquid diverter 21 has a flow restrictor outlet 29 sized to restrict the flow of secondary flow of milk 41 from the liquid diverter 21. The flow restrictor outlet 29 is not so small is to stop all flow of milk from the liquid diverter 21. When pulsed milk flow into the in-line sensor 10 halts, the liquid diverter 21 self-empties.

The liquid diverter 21 as shown is defined partly by a wall 30 of the elongated housing 20 itself and partly by a second wall section 31, the second wall section 31 located inside the elongated housing 20 so as to segregate off the liquid diverter 21 portion of the elongated housing 20 through which a secondary flow of milk 41 passes.

As shown in FIG. 7 and FIG. 8, in cross-section, about the location of the liquid diverter 21, the liquid receiver inlet 21 and flow direction of milk through the liquid diverter 21 may be co-axial with the longitudinal axis of the elongated housing 20. The liquid diverter 21 central longitudinal axis AA may however be offset relative to the central longitudinal axis BB of the elongated housing 20. For example, off-set to one side of the elongated housing 20. The liquid diverter 21 second wall section 31 may be a flat wall shape.

The flow restrictor outlet 24 may be a narrowed outlet from the liquid diverter 21 that slows the rate of flow of secondary flow of milk 41 from the liquid receiver outlet 24. The narrowed outlet 24 tapers in size/diameter from the liquid receiver inlet 22 to the exit point from the outlet 24. As noted in the description, the final size bb of the narrowed outlet 24 exit may vary depending on the nature of the pulsed milk flow and degree of residence time desired. The outlet 24 size bb may be around 8-12 times smaller than the overall elongated housing 20 width/diameter aa. The outlet 24 exit size bb may be approximately 3-5 times smaller than the liquid diverter 21 width/diameter cc.

The in-line sensor 10, except the sensor 23 itself, may be a single piece mould that a sensor 23 is attached to. The liquid diverter 21 detail described above may be integral to the single piece mould as well. Further, the in-line sensor 10 may be entirely passive and may have no moving parts.

EXAMPLE 3

The sequence of flow is shown further in FIGS. 9 to 16. The pulsed milk flow to the in-line sensor 10 may be un-even or pulsed with gaps in flow, yet the in-line sensor 10 is configured to always provide liquid to the sensor 23 to allow for even and continuous sensor 23 measurement. As may be appreciated, pulsed or un-even flows may result in air gaps that may cause sensed measurements to become unstable or give false readings. The in-line sensor 10 described avoids this by continuously always retaining at least some captured milk as secondary flow of milk 41 between pulses or un-even flow where the sensor 23 is located and a sensed measurement takes place, hence avoiding instability or false readings. As described however, once the residence time of the liquid diverter 21 is reached (timed with when a pulsed milk flow fully stops to the in-line sensor 10), the liquid receiver 21 fully drains or self-empties.

Figure 9:
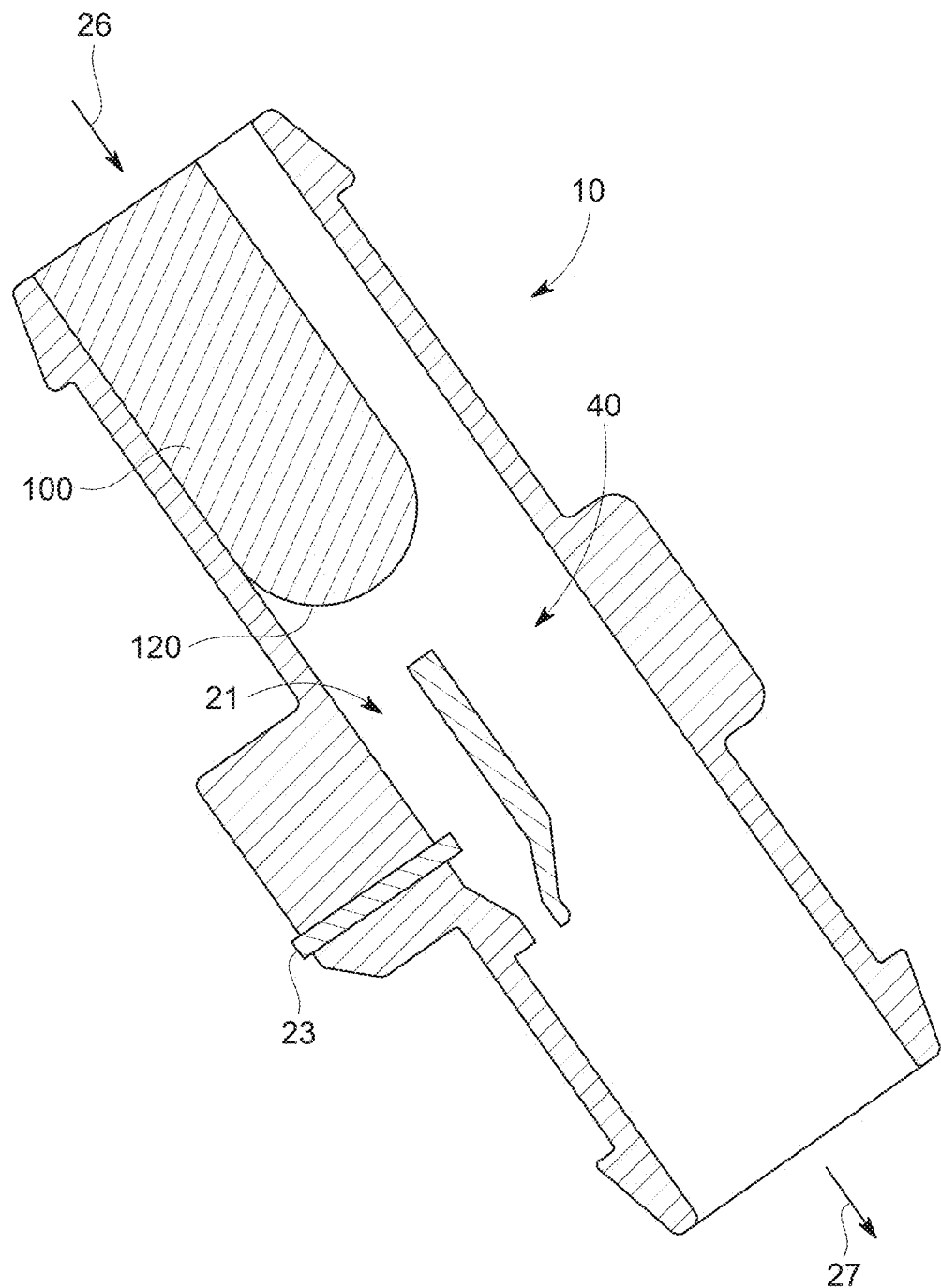
FIG. 9 illustrates the flow of liquid during a first phase of a first pulsation.
Figure 10:
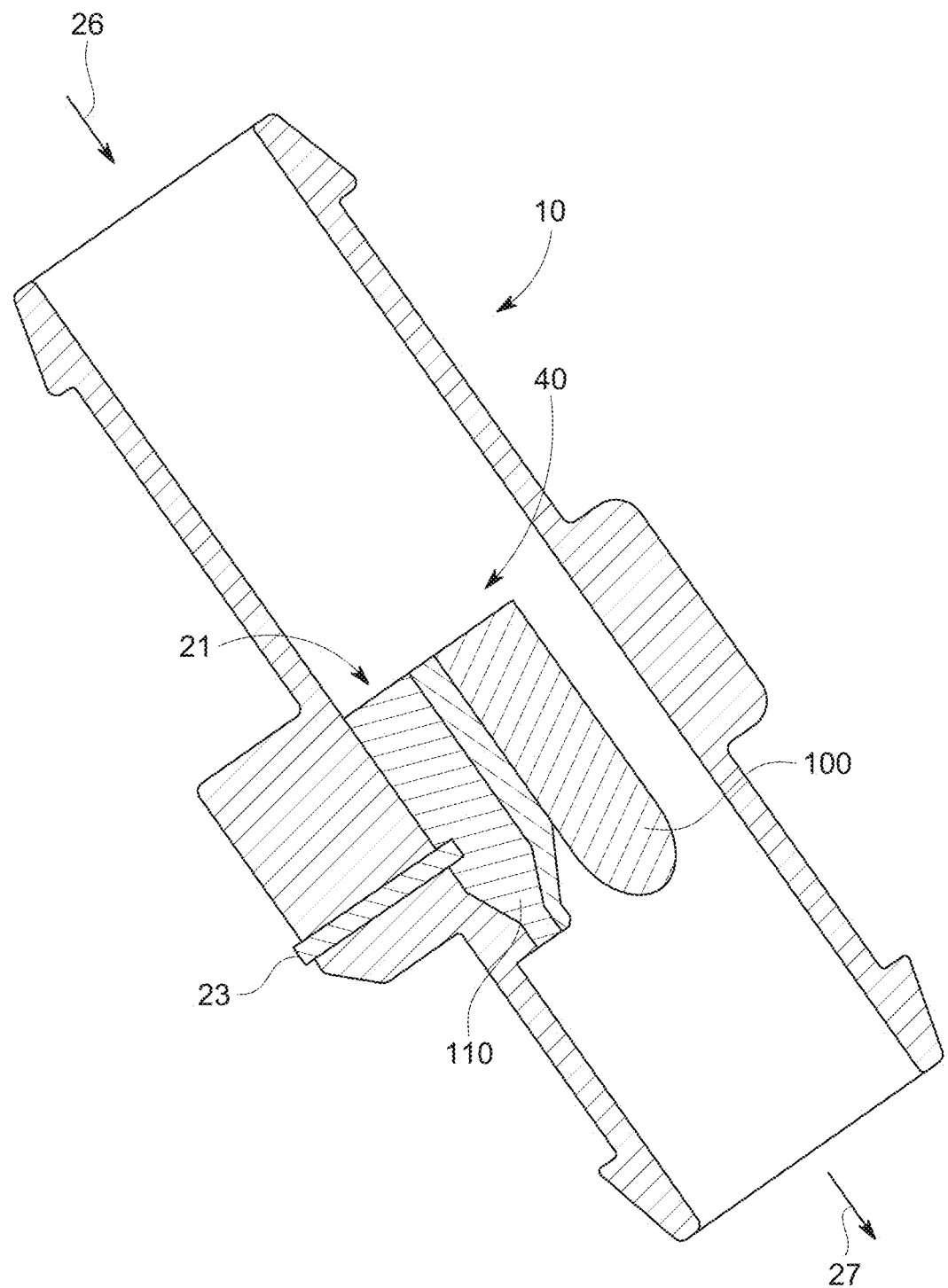
FIG. 10 illustrates a second phase of the first pulsation.
Figure 11:
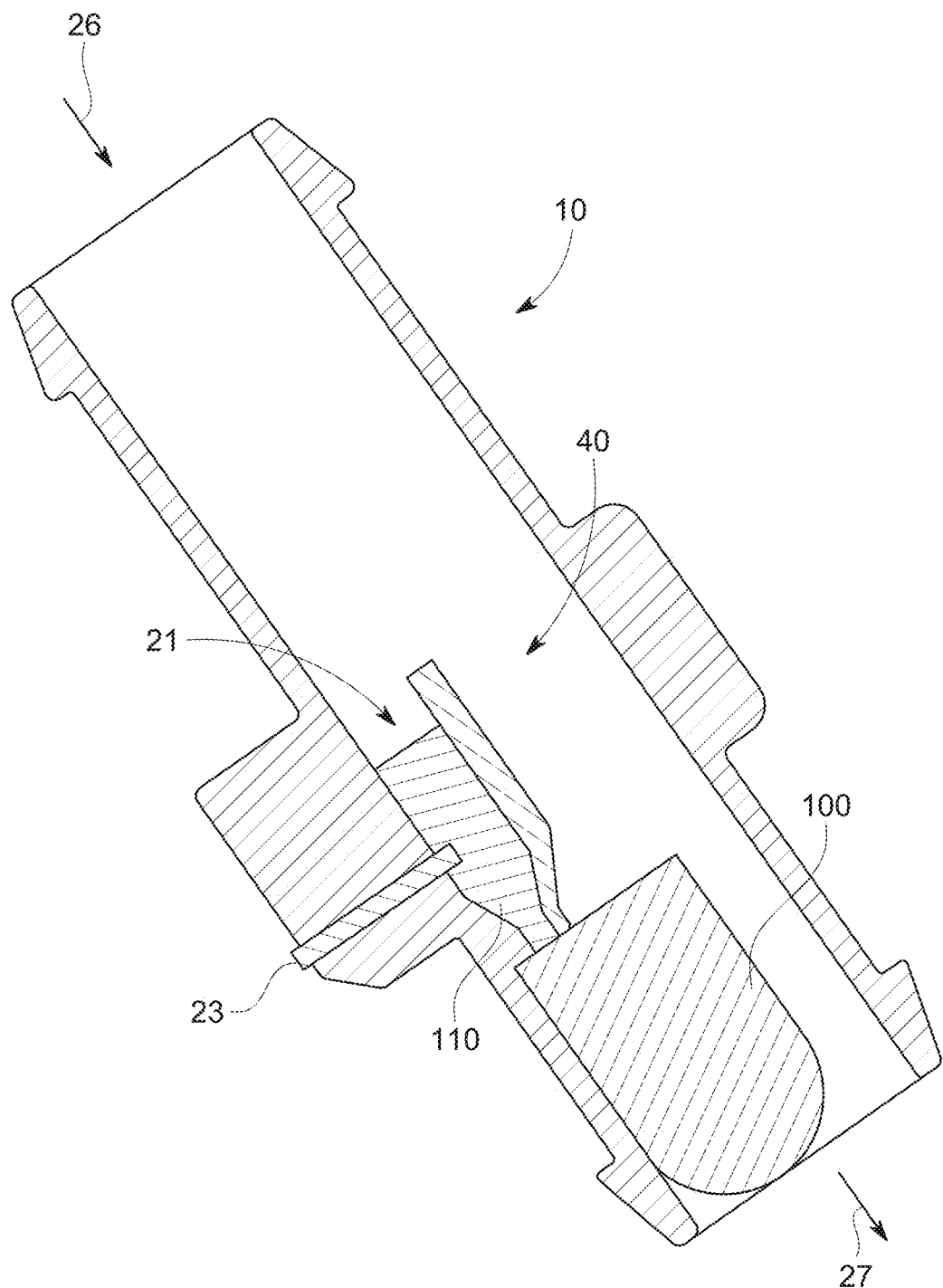
FIG. 11 illustrates a third phase of the first pulsation.

FIG. 9 shows the flow of a pulse of milk 100 during a first phase of a first pulsation. Milking machines typically have a pulsation of one pulsation per second. A slug (or pulse) of milk 100 (the pulsed milk flow 100 in this example) is pulled from the udder with each pulsation. The in-line sensor 10 is typically angled with the liquid diverter 21 and sensor 23 on the lower side of the elongated housing 20. In FIG. 10, a second phase of the first pulsation is shown where the milk pulse 100 reaches the central part of the in-line sensor 10 and fills both the liquid diverter 21 as captured milk or secondary flow of milk 110 and primary flow of milk 115 that passes on through the elongated housing 20. The liquid diverter 21 is preferentially filled by the foremilk 120 portion of the pulse of milk 100. The sensor 23 begins sensing the secondary flow of milk 110 property(ies). FIG. 11 shows a third phase of the first pulsation where the majority of the milk pulse 100 flows through the in-line sensor 10 as a primary flow of milk 115 and captured secondary flow of milk 110 left in the liquid diverter 21 flows slower due to the geometry of the flow restrictor outlet 24.

Figure 12:
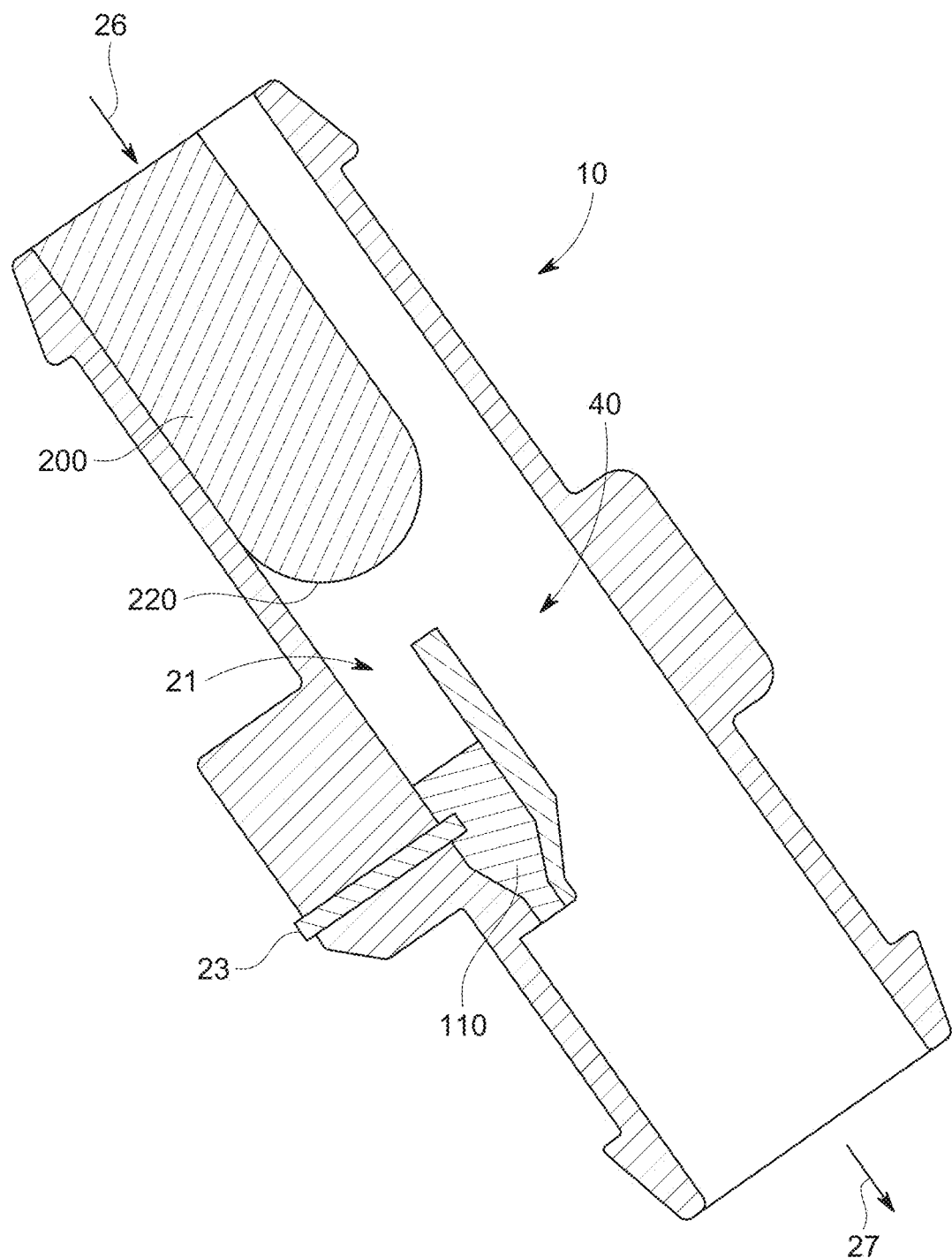
FIG. 12 illustrates a first phase of a second pulsation.
Figure 13:
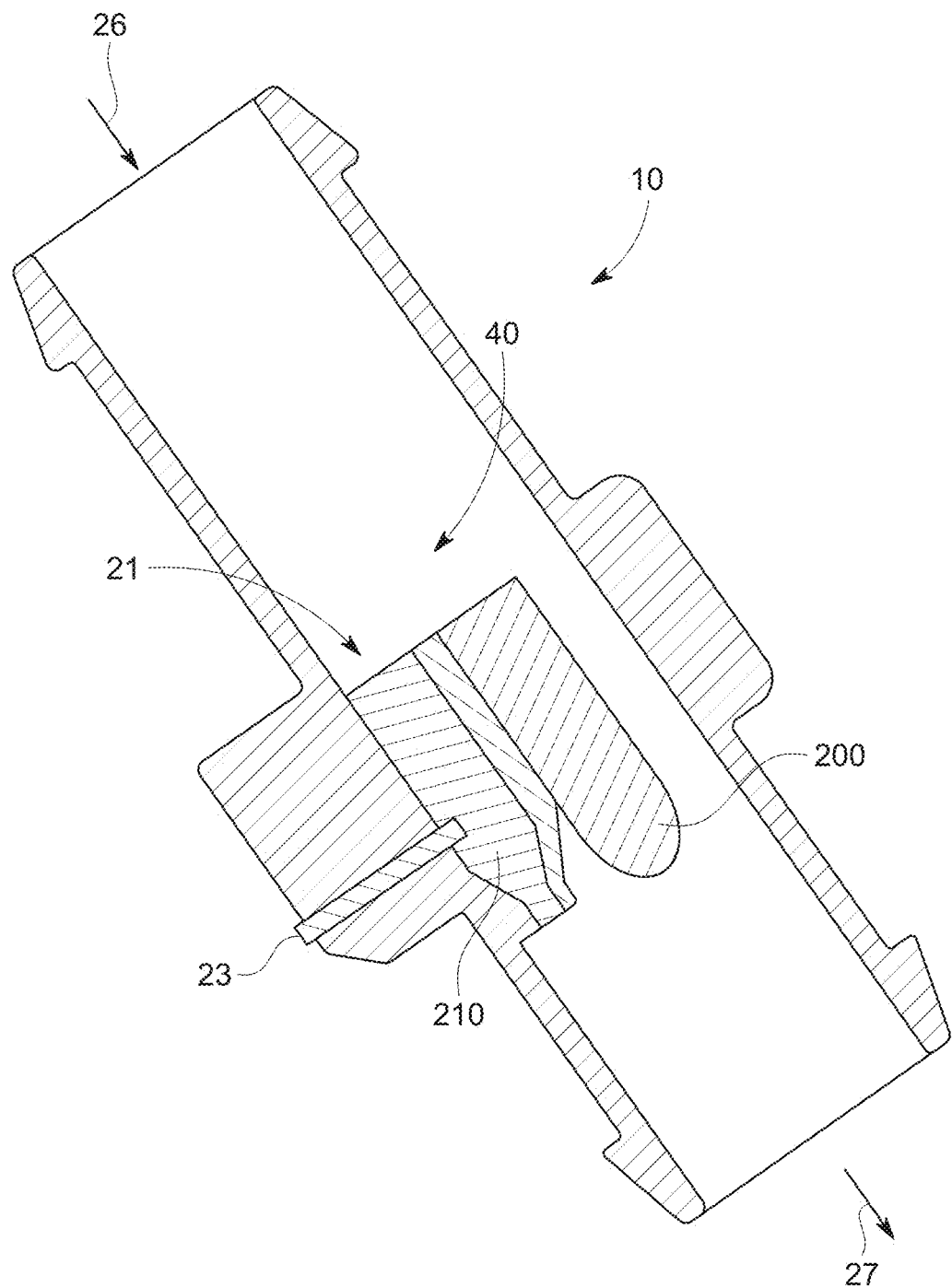
FIG. 13 illustrates a second phase of the second pulsation.
Figure 14:
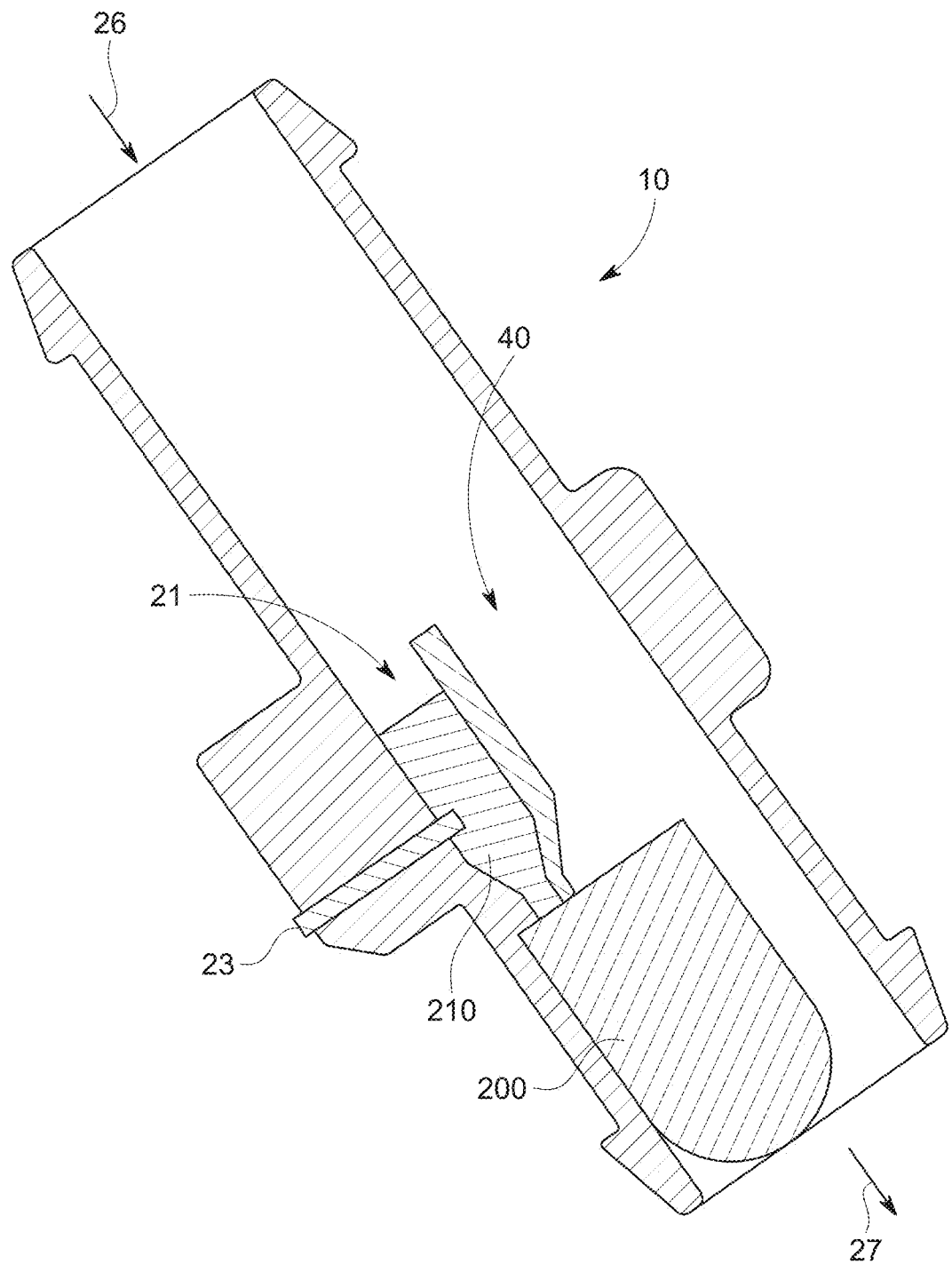
FIG. 14 illustrates the third phase of the second pulsation.

FIG. 12 shows a first phase of a second pulsation where a second milk pulse 200 enters the in-line sensor 10 while remnants of the first pulse 100 of captured secondary flow of milk 110 remain in the liquid diverter 21 which is still emptying. FIG. 13 shows a second phase of the second pulsation where the liquid diverter 21 is refilled by secondary flow of milk 210 captured from foremilk 220 of the second milk pulse 200 and primary flow of milk 215 of the second milk pulse 200 passes through the elongated housing 20. FIG. 14 shows the third phase of the second pulsation with some secondary flow of milk 210 captured in the liquid diverter 21 and the remaining primary flow of milk 215 of the second milk pulse 200 exiting the in-line sensor 10.

Figure 15:
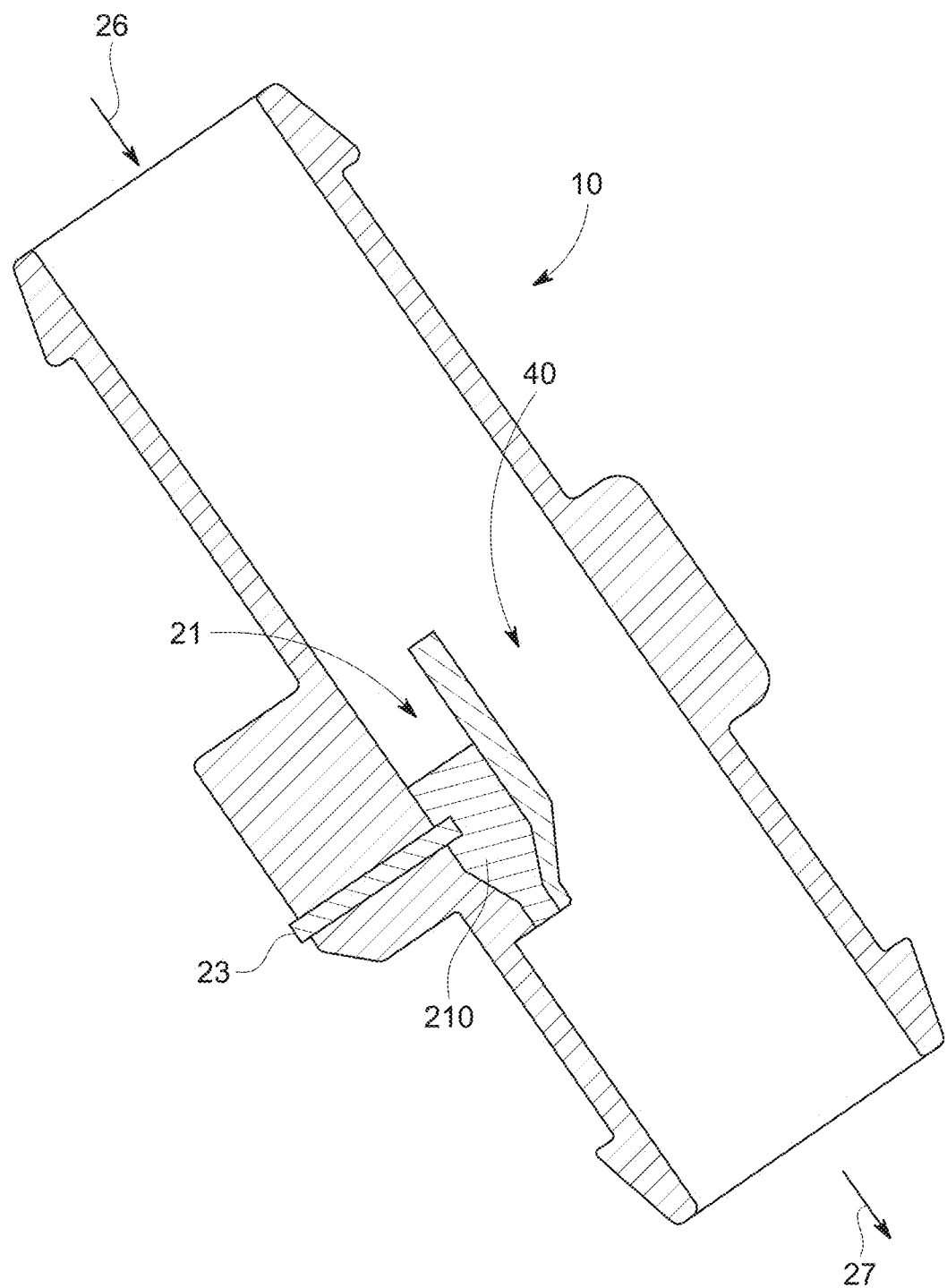
FIG. 15 illustrates a first phase of a final pulsation.

FIG. 15 shows a first phase of a final pulsation where the cow has finished milking and captured secondary flow of milk 210 empties out of the liquid diverter 21. The liquid diverter 21 self-empties so that captured secondary flow of milk 210 in the liquid diverter 21 self-empties and drains fully when pulsed milk flow 100, 200 ceases through the elongated housing 20. Reference is made to a first or second pulsed milk flow 100, 200 but in practice there may be hundreds or thousands of milk pulses passing through the in-line sensor 10 and the second milk pulse 200 may be repeated multiple times until milking is complete and no further milk pulses 100, 200 are received by the in-line sensor 10 hence when this final pulsation phase begins.

Figure 16:
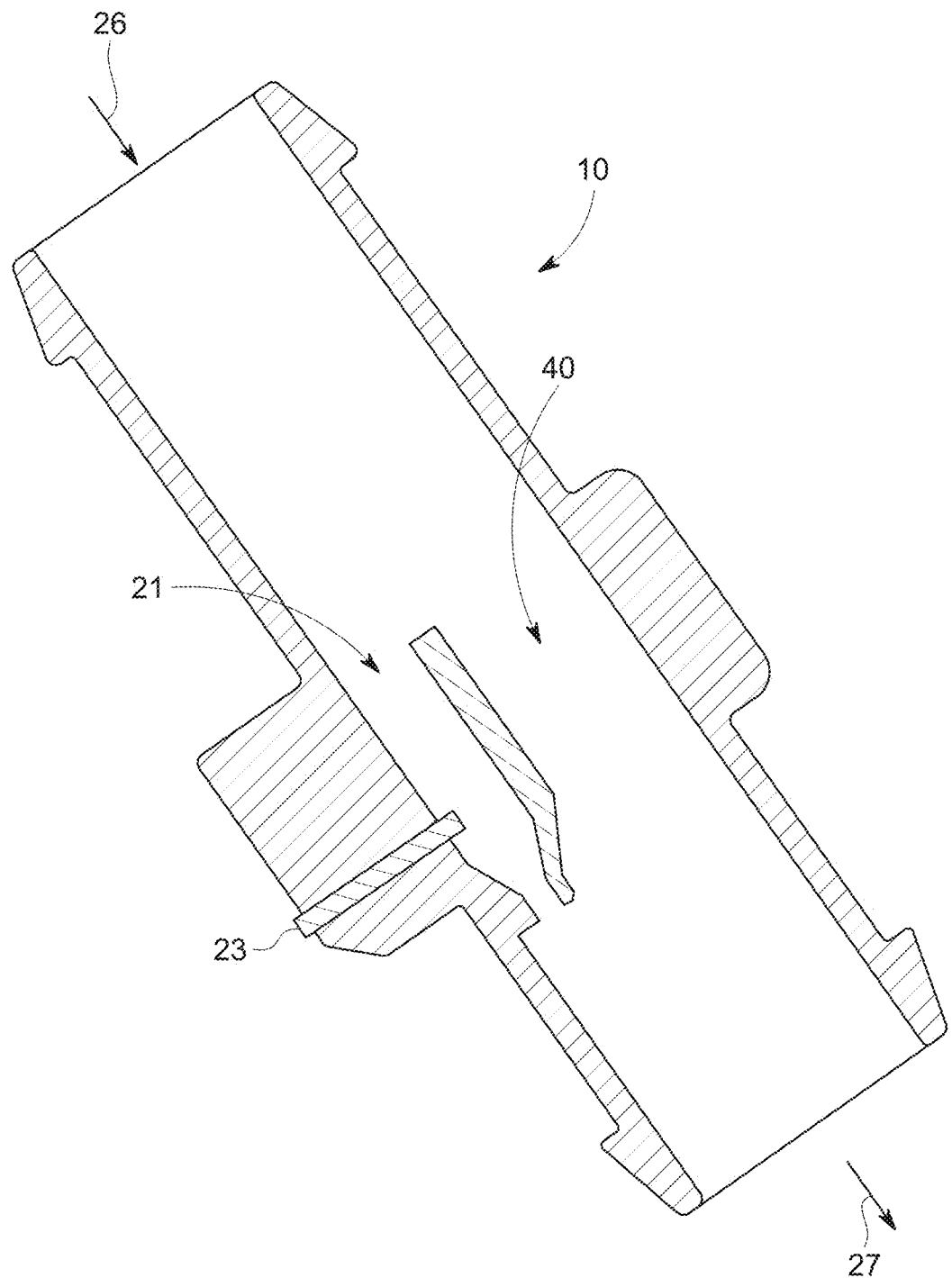
FIG. 16 illustrates the second phase of final pulsation.

FIG. 16 shows the second phase of final pulsation with the liquid diverter 21 now empty and drained of any milk residue. The change from milk to air in the liquid diverter 21 is sensed by the sensor 23 indicating the end of milking.

The majority of the pulsed milk flow 100, 200 (60, or 70, or 80, or 90, or 95% by volume) moves directly through the elongated housing 20 as a primary flow of milk 40, 115, 215 and does not pass through the liquid diverter 21.

Secondary flow of milk 41, 110, 210 being captured and passing through the liquid diverter 21 moves through the elongated housing 20 at a slower flow rate than primary flow of milk 40, 115, 215 through the elongated housing 20. The liquid diverter 21 is configured to have a residence time for captured milk in the liquid diverter 21 so as to slow emptying of the liquid diverter 21. This residence time may range from 1 second to 10 minutes depending on the application to which the in-line sensor 10 is used. It should be noted that no consideration is made to address foaming or aeration of milk flow in the in-line sensor 10. This is because, in the inventor's experience, no or negligible foaming or aeration occurs when milk flows through the in-line sensor 10 described due to the in-line sensor 10 design and configuration.

EXAMPLE 4

Figure 17:
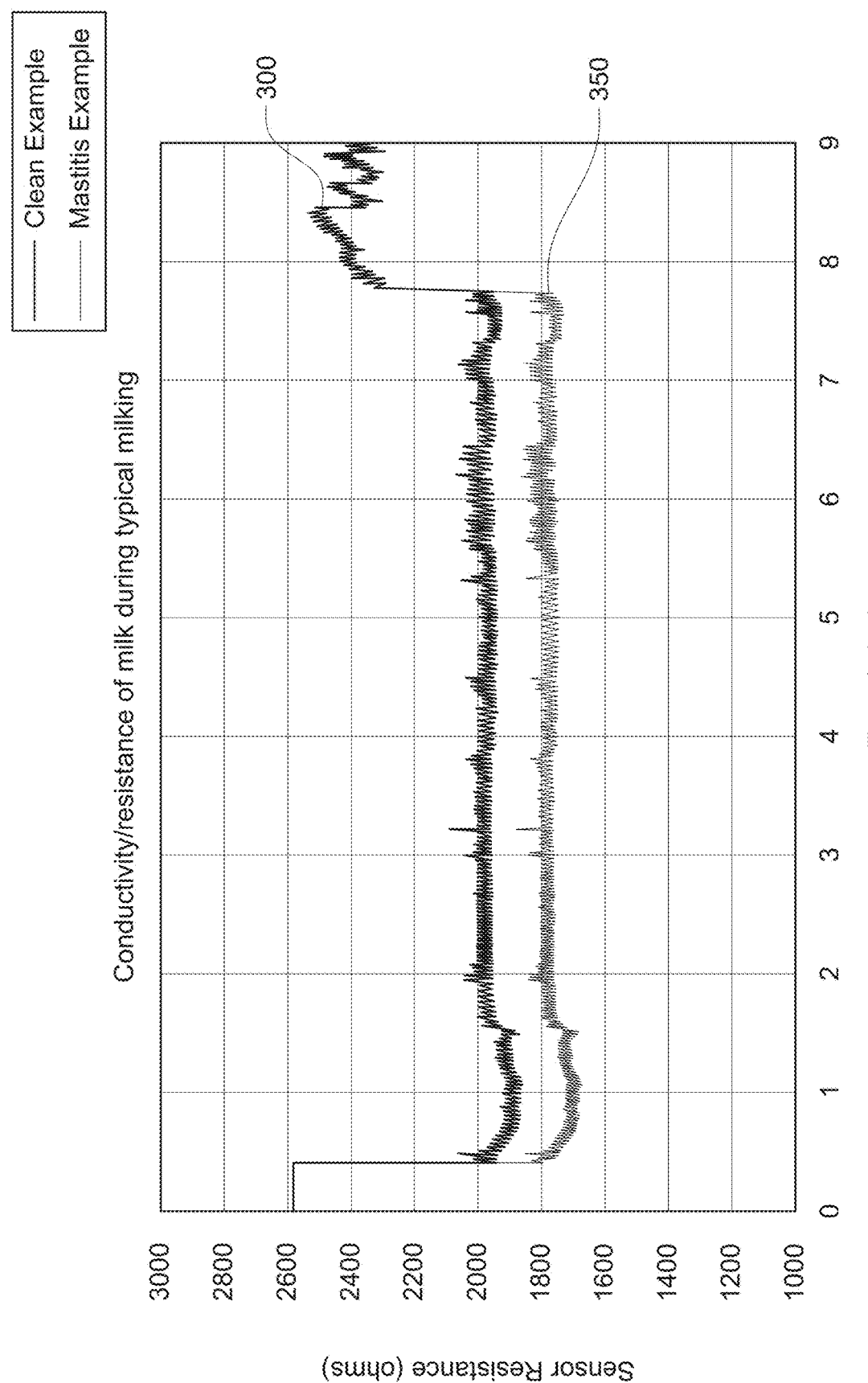
FIG. 17 illustrates a graph showing the conductivity readings taken for milk passing through the in-line sensor where the upper line shows conductivity values recorded for a clean (non-mastitis affected) milk with a normal or absence of somatic cells and the second or lower line shows the measured values for a mastitis affected sample.

In this example, the way a sensed property is measured is shown with reference to FIG. 17. To show how the in-line sensor 10 operates and the absence of air in the sensed region of milk, conductivity readings were taken of the milk according to the sequence of flow described in Example 3 above. The upper line 300 shown in FIG. 17 are conductivity values recorded for a clean (non-mastitis affected) milk with a normal or absence of somatic cells. The conductivity measured in terms of resistance drops once milk enters the liquid diverter 21 being the reading at time 0.5 min on the left of FIG. 17 and then remains stable for the following time period during milking when multiple pulsations occur indicating a continuous secondary flow of milk 41, 110, 210 into and through the liquid diverter 21. When milking ceased at time 7.8 min approximately, the conductivity immediately changes shown as a resistance change as the liquid diverter 21 empties and the sensor 23 begins measuring the resistance of air in the liquid diverter 21.

By way of illustration, it can be seen from FIG. 17 how, when somatic cells are present in the milk (from a mastitis infection), the resistance drops (lower line 350) as conductivity of the milk increases due to the presence of the somatic cells.

There is a clear step change between a 'normal' milk without somatic cells and a mastitis infected milk source meaning it is easy for a person or processor to spot a divergent sensed parameter and hence raise an alert. Because the in-line sensors 10 described are located immediately after milk collection from a quarter, the infected animal can be rapidly identified and even the infected teat or quarter identified as well.

EXAMPLE 5

Figure 18:
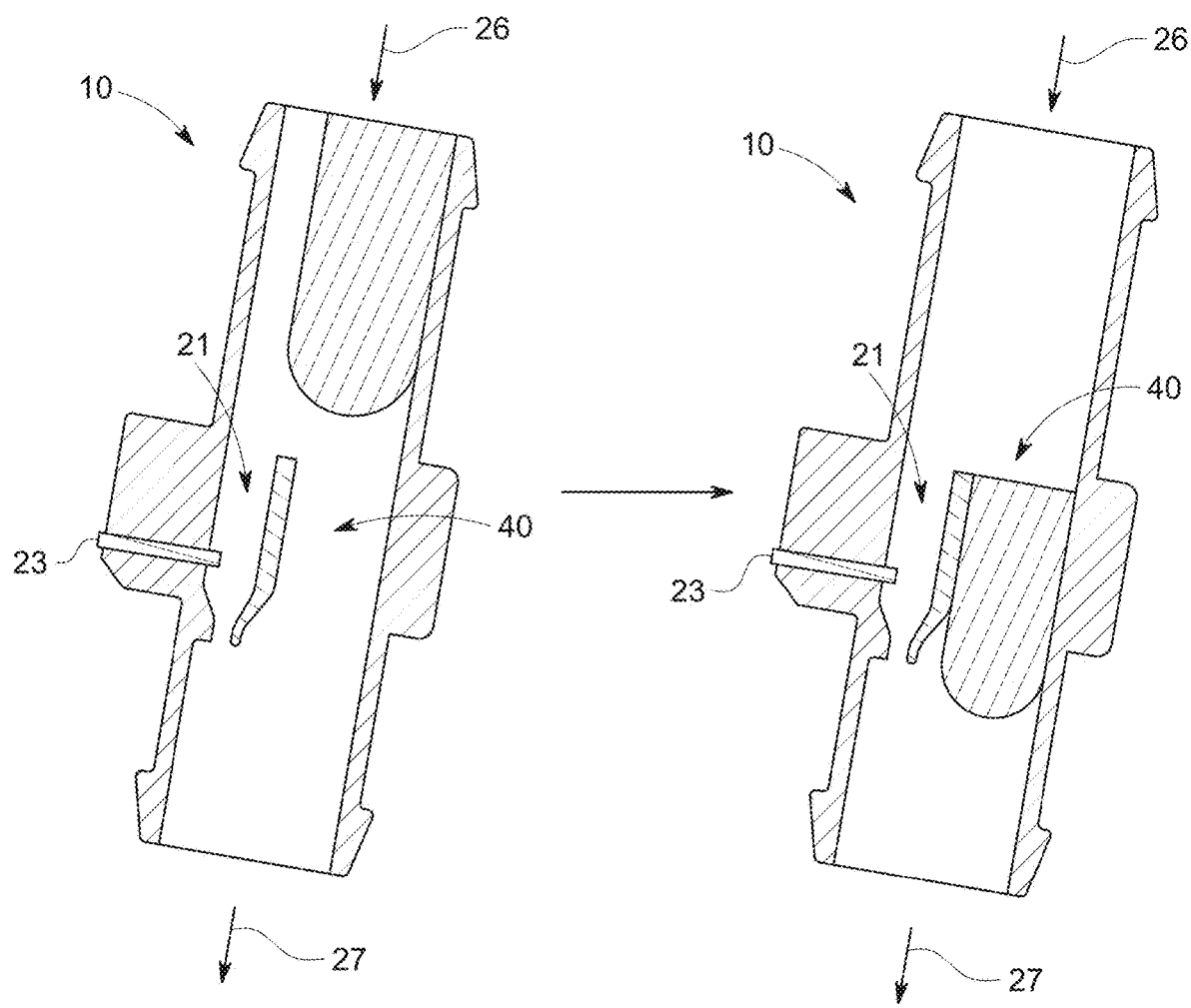
FIG. 18 illustrates a cross-section view of the in-line sensor with the liquid diverter at an elevated position relative to the pulsed milk flow.

As shown in the above examples, the liquid diverter 21 may be positioned at a low or downwards side of the in-line sensor 10 i.e. to use gravity force to assist or urge pulsed milk flow 100, 200 at least partly through the liquid diverter 21 and elongated housing 20. If the liquid diverter 21 were at an elevated position relative to the pulsed milk flow 100, 200 through the elongated housing like that shown in FIG. 18, it may be possible for the liquid diverter 21 to not fill, or not fill and empty, in a continuous manner.

In the inventor's experience, the liquid diverter 21 need not be directly below the main pulsed milk flow 100, 200. The sensor 23 and the liquid diverter 21 may be angled relative to a horizontal plane by as much as 60, or 70, or 80 degrees relative to a horizontal plane and pulsed milk flow 100, 200 will still flow uniformly and continuously through the in-line sensor 10 and liquid diverter 21.

Figure 19:
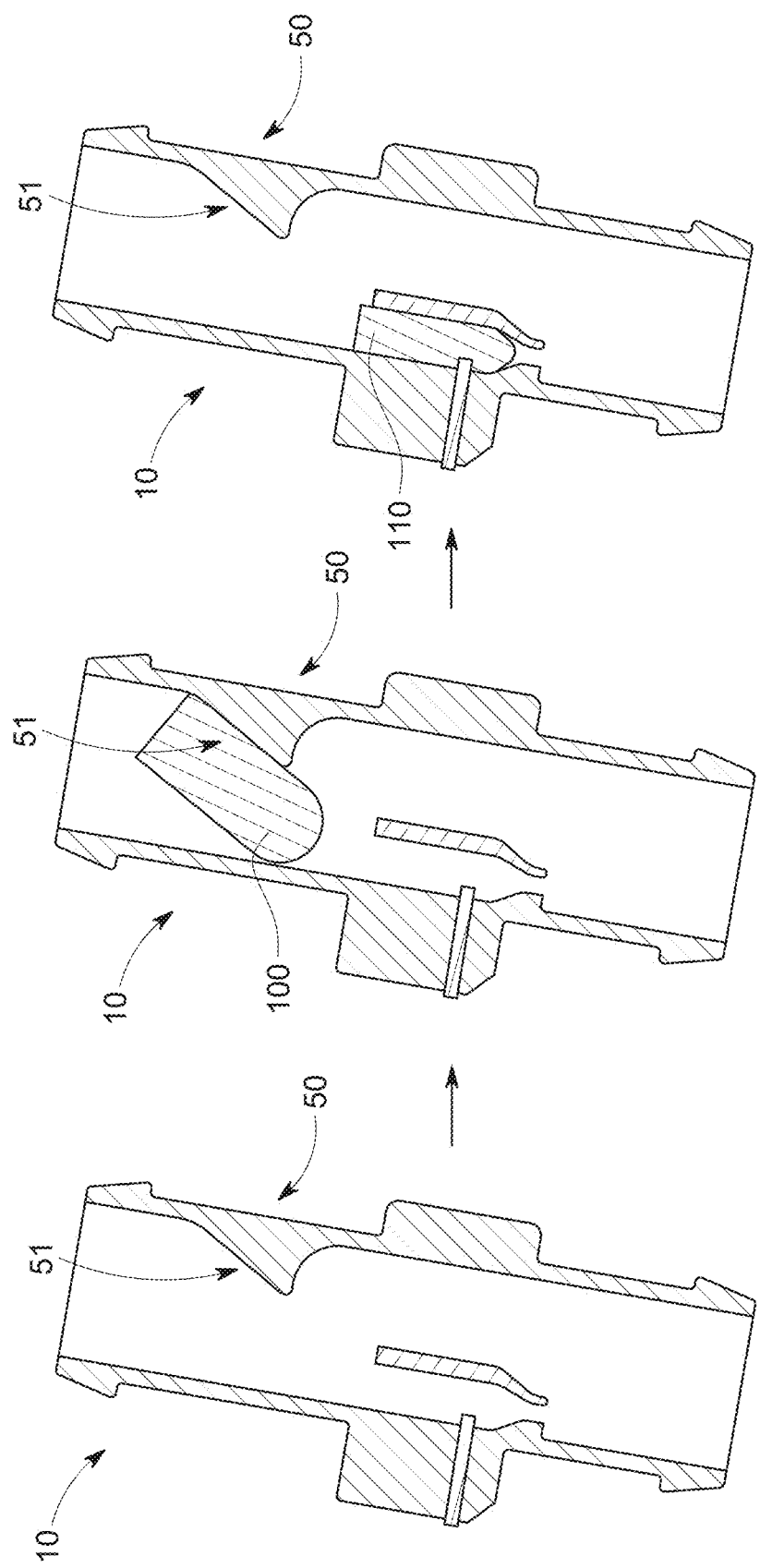
FIG. 19 illustrates a cross-section view of an alternative embodiment in-line sensor where the internal wall of the housing comprises a ramp upstream of the liquid diverter inside the housing.
Figure 20:
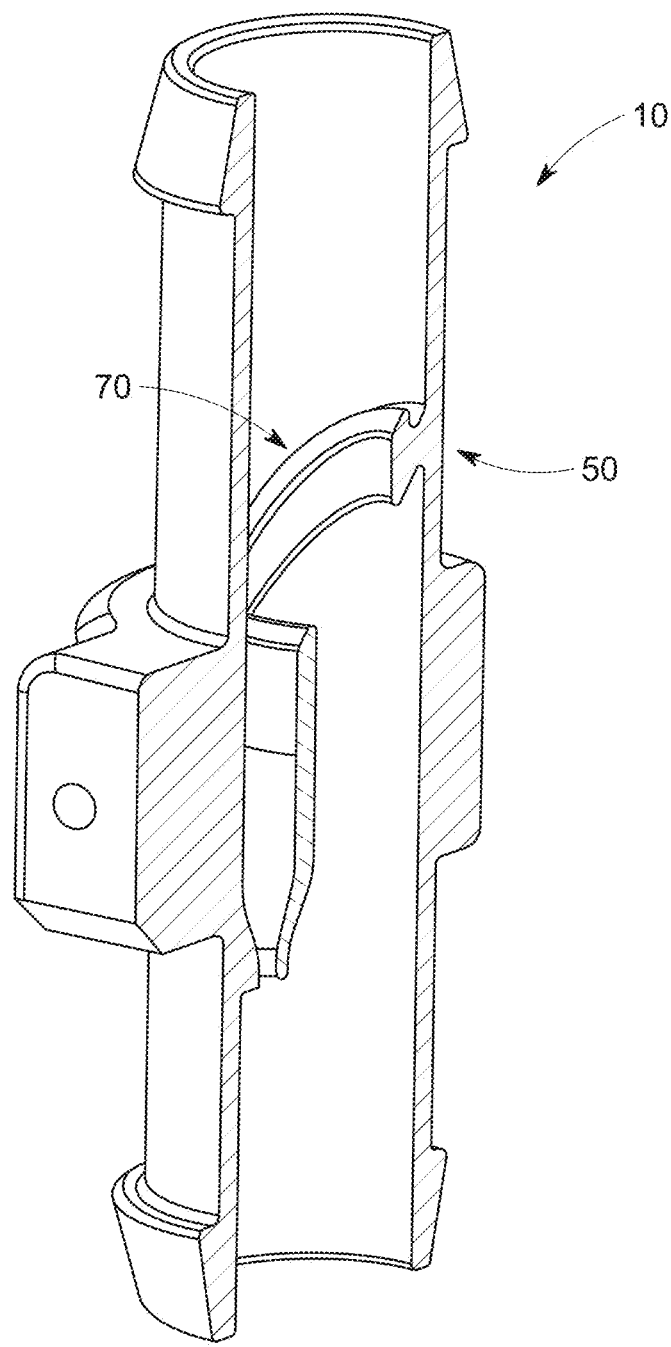
FIG. 20 illustrates a perspective section view of a further alternative embodiment of in-line sensor where a gutter is included around the internal surface of the sensor body, upstream of the liquid diverter.
Figure 21:
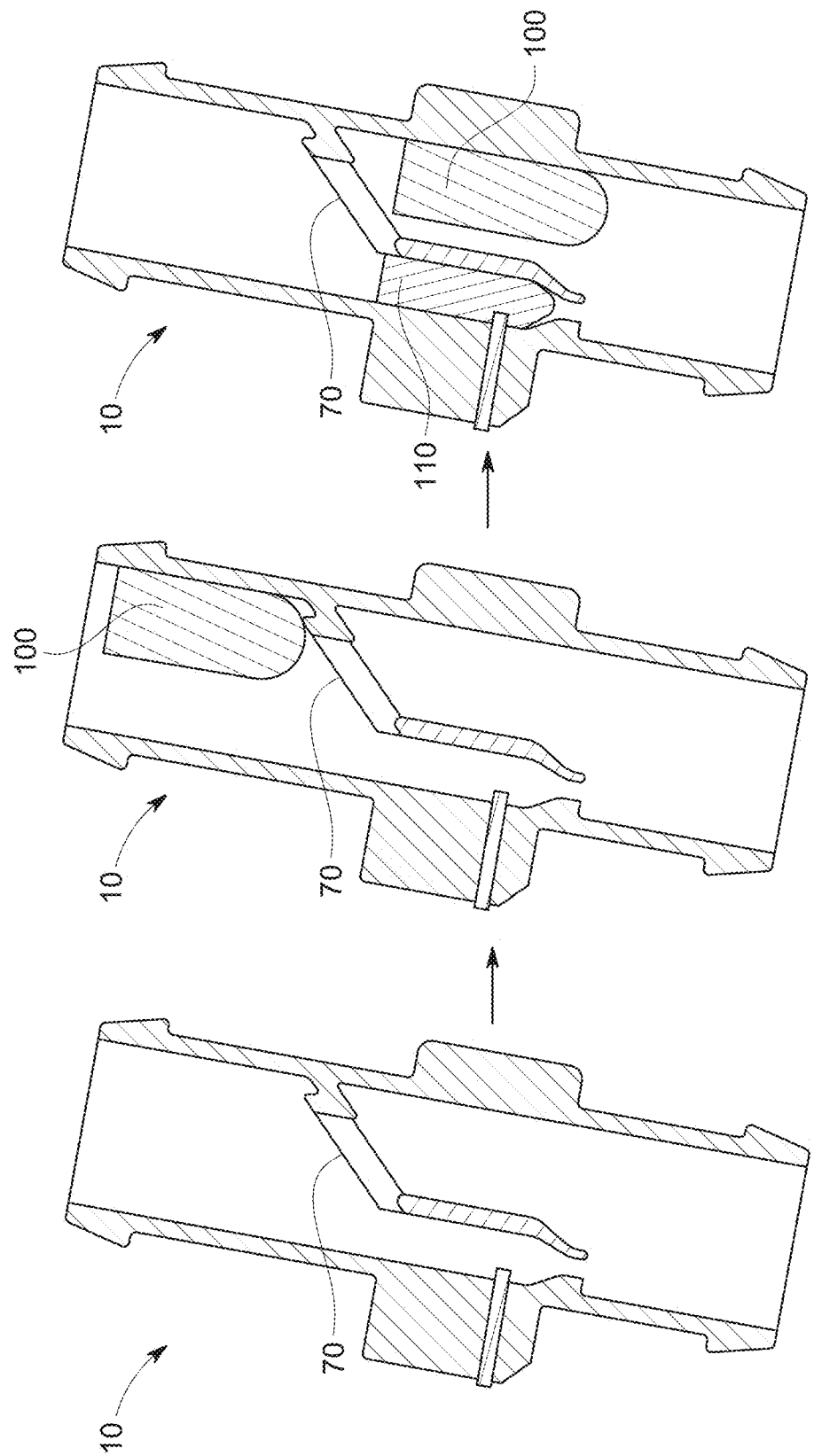
FIG. 21 illustrates the above embodiment with pulsed milk flow through the in-line sensor.

Alternative embodiments may be used where the liquid diverter 21 is not on a low side of the in-line sensor 10. FIGS. 19-21 illustrate alternative embodiments where the in-line sensor 10 may comprise at least one flow diverting mechanism 50 that urges pulsed milk flow 100, 200 towards the liquid diverter 21.

For example, as shown in FIG. 19, the internal wall of the elongated housing 20 may comprise a ramp or ramps 51 upstream of the liquid diverter 21 inside the elongated housing 20 that act to re-direct some or all of the pulsed milk flow 100, 200 towards the liquid diverter 21. The high velocity of the pulsed milk flow 100, 200 entering the in-line sensor 10 means that the ramp or ramps 51 eject pulsed milk flow 100, 200 from one side of the elongated housing 20 to the other side of the elongated housing 20 and hence towards the liquid diverter 21 for partial separation into a secondary flow of milk 41, 110, 210 and a primary flow of milk 40, 115, 215.

An alternative embodiment is shown in FIG. 20 and FIG. 21 where a gutter 70 is included around the internal surface of the in-line sensor 10 elongated housing 20, upstream of the liquid diverter 21. Pulsed milk flow 100, 200 flowing on the other side of the elongated housing 20 is directed via the gutter 70 into the liquid diverter 21.

Figure 22:
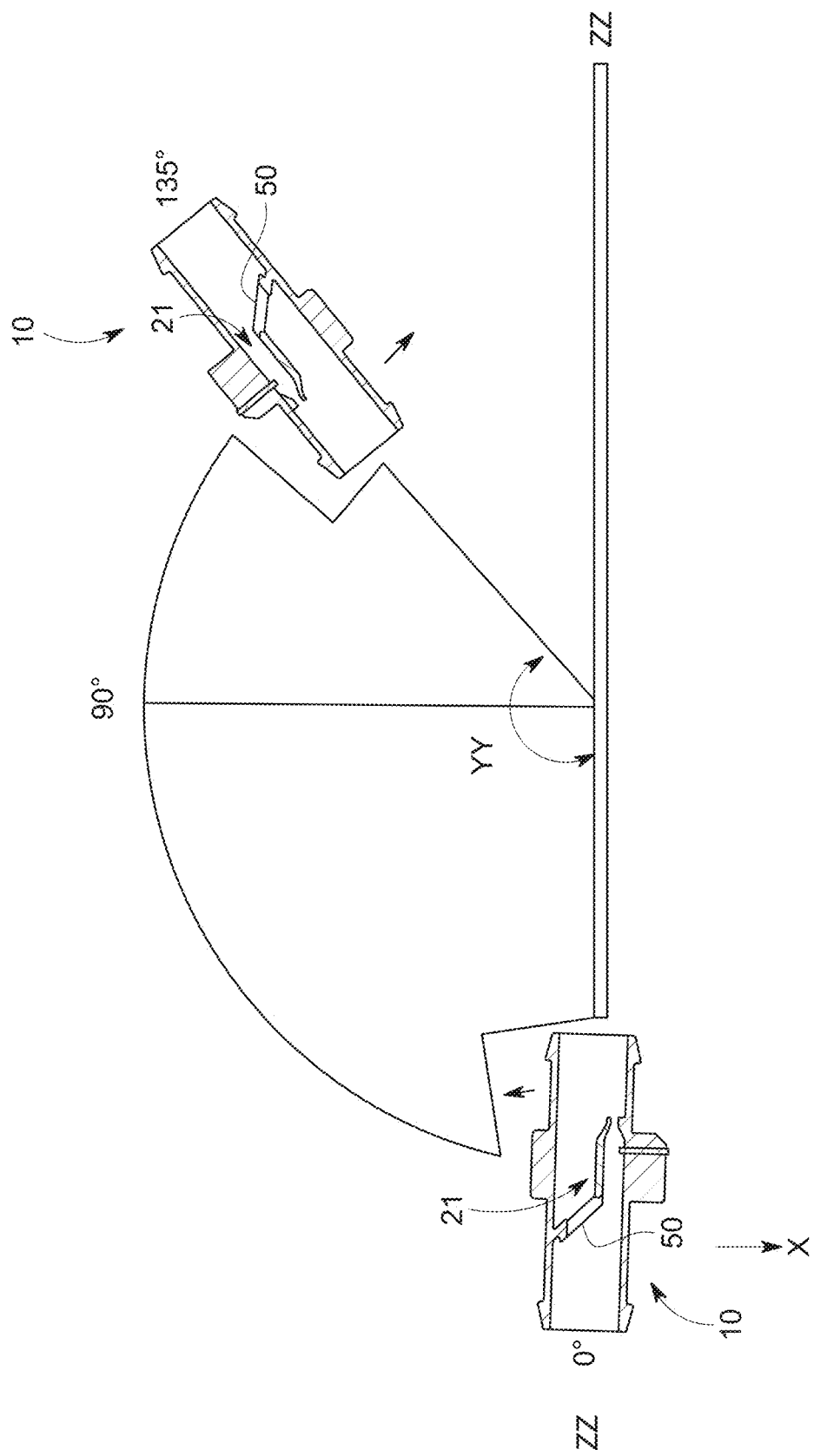

FIG. 22 illustrates the range of working angles that the in-line sensor may be used in. As noted elsewhere in this description, the liquid diverter 21 may be located on a low or downwards side X of the in-line sensor 10 in use i.e. the in-line sensor 10 is positioned at an angle YY relative to a horizontal plane ZZ from 60 degrees to approximately 80 degrees. If the flow diverting mechanism 50 is used like that described in this example, the working range for the angle YY may be as far as 0 to 90 degrees as illustrated in FIG. 22.

Aspects of the in-line sensor, milking cluster and associated methods have been described by way of example only and it should be appreciated that modifications and additions may be made thereto without departing from the scope of the claims herein.

What is claimed is:

1. An in-line sensor configured to measure a sensed property of milk collected from a lactating animal, the in-line sensor comprising:
an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with said pulsed milk flow through the elongated housing; and
a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing and wherein the liquid diverter is configured to capture and measure characteristics of a foremilk portion of each pulse of the pulsed milk flow passing through the in-line sensor;
wherein the liquid diverter comprises:
a liquid receiver inlet that receives the secondary flow of milk therein;
a sensor measuring a property of the secondary flow of milk received in the liquid receiver inlet;
a flow restrictor outlet configured to restrict a flow rate of the secondary flow of milk from the liquid diverter;
wherein the liquid diverter is configured to:
in use, be aligned so that the liquid receiver inlet is positioned generally above the flow restrictor outlet;
retain said secondary flow of milk about the sensor between pulses of the pulsed milk flow to the in-line sensor; and
when the pulsed milk flow ceases through the in-line sensor, said secondary flow of milk retained about the sensor, self-empties and drains fully via gravity from the liquid diverter via the flow restrictor outlet; and,
wherein the liquid diverter is offset to one side of the elongated housing so as to be offset relative to said primary flow of said pulsed milk flow through the elongated housing.

2. The in-line sensor as claimed in claim 1 wherein the in-line sensor is entirely passive and has no moving parts.

3. The in-line sensor as claimed in claim 1 wherein the sensor communicates directly with milk in the liquid receiver inlet and wherein the sensor does not slow or hinder self-emptying of milk from the liquid diverter.

4. The in-line sensor as claimed in claim 1 wherein the elongated housing is configured to minimise foaming or aeration of the pulsed milk flow therethrough by interfering with a minority of the pulsed milk flow through the elongated housing, the majority of the pulsed milk flow flowing as a primary flow of milk through the elongated housing without being diverted in flow direction.

5. The in-line sensor as claimed in claim 1 wherein:
the primary flow of milk through the elongated housing and the secondary flow of milk through the liquid diverter flow in a coaxial direction along a longitudinal axis of the elongated housing; and
the primary flow of milk and the secondary flow of milk are offset from each other in a direction orthogonal to the longitudinal axis of the primary flow of milk and the secondary flow of milk.

6. The in-line sensor as claimed in claim 1 wherein the elongated housing and the liquid diverter are a single piece mould that a sensor is attached to.

7. The in-line sensor as claimed in claim 1 wherein the elongated housing is located at an angle relative to a horizontal plane parallel to a ground and the liquid diverter is positioned within the elongated housing to be on a lower side of the in-line sensor.

8. The in-line sensor as claimed in claim 7 wherein the elongated housing, in use, is angled at 60 to 80 degrees relative to a horizontal plane parallel to the ground.

9. The in-line sensor as claimed in claim 1 wherein the in-line sensor further comprises at least one flow diverting element that urges at least part of the pulsed milk flow towards the liquid diverter.

10. The in-line sensor as claimed in claim 9 wherein the elongated housing, in use, is angled at 0 to 90 degrees relative to a horizontal plane parallel to a ground.

11. The in-line sensor as claimed in claim 9 further comprising a diverting element located distant to a low side of the elongated housing.

12. The in-line sensor as claimed in claim 1 wherein the secondary flow of milk passing through the liquid diverter moves at a slower flow rate than a flow rate of the primary flow of milk moves through the elongated housing.

13. The in-line sensor as claimed in claim 1 wherein the liquid receiver inlet of the liquid diverter is configured so that a rate of draining of said secondary flow of milk from the liquid diverter is sufficiently slow to retain at least some milk from each pulse of pulsed milk flow passing through the in-line sensor in the liquid diverter between pulses of the pulsed milk flow to the in-line sensor.

14. The in-line sensor as claimed in claim 1 wherein the sensor measures characteristics of the pulsed milk flow selected from: conductivity, temperature, presence or absence of chemical or bio-chemical marker(s), liquid colour/optical properties, clarity/turbidity, milk flow rate, and combinations thereof.

15. The in-line sensor as claimed in claim 1 wherein the in-line sensor is configured to sense mastitis in the pulsed milk flow to the in-line sensor by measuring a conductivity of the secondary flow of milk as the secondary flow of milk passes through the liquid diverter and past the sensor.

16. A milking cluster for pulsed milk flow collection comprising:
two or more milking cups and a claw, the two or more milking cups each configured to connect to and directing pulsed milk flows from each of the two or more milking cups to the claw, the claw configured to receive and mix the pulsed milk flows; and,
an in-line sensor intermediate to each milking cup of said two or more milking cups and intermediate to the claw,
wherein each in-line sensor of said in-line sensor intermediate to said each milking cup and said claw comprises
an elongated housing with an inlet configured to receive a pulsed milk flow from a milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with said pulsed milk flow through the elongated housing; and
a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing and wherein the liquid diverter is configured to capture and measure characteristics of a foremilk portion of each pulse of the pulsed milk flow passing through the in-line sensor;
wherein the liquid diverter comprises:
a liquid receiver inlet that receives the secondary flow of milk therein;
a sensor measuring a property of the secondary flow of milk received in the liquid receiver inlet;
a flow restrictor outlet configured to restrict a flow rate of the secondary flow of milk from the liquid diverter;
wherein the liquid diverter is configured to:
in use, be aligned so that the liquid receiver inlet is positioned generally above the flow restrictor outlet;
retain said secondary flow of milk about the sensor between pulses of the pulsed milk flow to the in-line sensor; and
when the pulsed milk flow ceases through the in-line sensor, said secondary flow of milk retained about the sensor, self-empties and drains fully via gravity from the liquid diverter via the flow restrictor outlet; and,
wherein the liquid diverter is offset to one side of the elongated housing so as to be offset relative to said primary flow of said pulsed milk flow through the elongated housing;
wherein said each in-line sensor is configured to sense a characteristic of the pulsed milk flow from an individual milking cup prior to mixing of the pulsed milk flow in the claw.

17. A method of sensing a property or a characteristic of a pulsed milk flow, comprising:
providing a pulsed milk flow from a milking cup to an in-line sensor configured to measure a sensed property of milk collected from a lactating animal, wherein said in-line sensor comprises
an elongated housing with an inlet configured to receive said pulsed milk flow from said milking cup and an outlet configured to discharge the pulsed milk flow from the elongated housing to a claw, the elongated housing being continuous and straight and which directs the pulsed milk flow from the inlet to the outlet, the inlet, in use, being positioned generally above the outlet to allow gravity to assist with said pulsed milk flow through the elongated housing; and
a liquid diverter inside the elongated housing, the liquid diverter configured to split the pulsed milk flow through the elongated housing into a primary flow of milk through the elongated housing and a secondary flow of milk through the liquid diverter, the liquid diverter configured to capture less than 40% by volume of a total pulsed milk flow through the in-line sensor as the secondary flow into the liquid diverter, a majority of the total pulsed milk flow through the in-line sensor moving as an unimpeded primary flow of milk through the elongated housing and wherein the liquid diverter is configured to capture and measure characteristics of a foremilk portion of each pulse of the pulsed milk flow passing through the in-line sensor;
wherein the liquid diverter comprises:
a liquid receiver inlet that receives the secondary flow of milk therein;
a sensor measuring a property of the secondary flow of milk received in the liquid receiver inlet;
a flow restrictor outlet configured to restrict a flow rate of the secondary flow of milk from the liquid diverter;
wherein the liquid diverter is configured to:
in use, be aligned so that the liquid receiver inlet is positioned generally above the flow restrictor outlet;
retain said secondary flow of milk about the sensor between pulses of the pulsed milk flow to the in-line sensor; and when the pulsed milk flow ceases through the in-line sensor, said secondary flow of milk retained about the sensor, self-empties and drains fully via gravity from the liquid diverter via the flow restrictor outlet; and, wherein the liquid diverter is offset to one side of the elongated housing so as to be offset relative to said primary flow of said pulsed milk flow through the elongated housing; and passing the pulsed milk flow through the in-line sensor and receiving sensed characteristics of the pulsed milk flow from the in-line sensor.

18. The method of sensing a property or a characteristic of a pulsed milk flow as claimed in claim 17, further comprising sensing said characteristic of a single teat pulsed milk flow in a milking cluster comprising at least said milking cup prior to mixing of multiple pulsed milk flows from multiple teats by, installing, intermediate to each milking cup of said milking cluster and said claw in the milking cluster, said in-line sensor;

providing said multiple pulsed milk flows from said each milking cup to each of said in-line sensor; and passing the multiple pulsed milk flows through each of said in-line sensor and receiving said sensed characteristics of each pulsed milk flow of said multiple pulsed milk flows in each of said in-line sensor.

\* \* \* \* \*